United States Patent
Justin et al.

(10) Patent No.: US 7,951,412 B2
(45) Date of Patent: May 31, 2011

(54) LASER BASED METAL DEPOSITION (LBMD) OF ANTIMICROBIALS TO IMPLANT SURFACES

(75) Inventors: Daniel F. Justin, Logan, UT (US); Brent E. Stucker, River Heights, UT (US); Durga Janaki Ram Gabbita, Logan, UT (US); David William Britt, Mendon, UT (US)

(73) Assignee: MedicineLodge Inc., Logan, UT (US)

( * ) Notice: Subject to any disclaimer, the term of this patent is extended or adjusted under 35 U.S.C. 154(b) by 1110 days.

(21) Appl. No.: 11/624,041

(22) Filed: Jan. 17, 2007

(65) Prior Publication Data

US 2007/0287027 A1    Dec. 13, 2007

Related U.S. Application Data

(60) Provisional application No. 60/811,934, filed on Jun. 7, 2006.

(51) Int. Cl.
*B05D 3/00* (2006.01)
*C21D 1/09* (2006.01)
*B32B 15/00* (2006.01)

(52) U.S. Cl. ........ 427/2.1; 427/2.24; 427/2.25; 428/615; 148/525; 148/526

(58) Field of Classification Search .......... 427/2.1–2.31, 427/596, 597; 428/615; 148/525, 526
See application file for complete search history.

(56) References Cited

U.S. PATENT DOCUMENTS

| | | |
|---|---|---|
| 3,947,653 A | 3/1976 | Fairbairn |
| 4,048,459 A | 9/1977 | Earle et al. |
| 4,117,302 A | 9/1978 | Earle et al. |
| 4,200,669 A | 4/1980 | Schaefer et al. |
| 4,218,494 A | 8/1980 | Belmondo et al. |
| 4,243,867 A | 1/1981 | Earle et al. |
| 4,269,868 A | 5/1981 | Livsey |
| 4,284,443 A | 8/1981 | Hilton |
| 4,289,952 A | 9/1981 | Haggerty |
| 4,299,860 A | 11/1981 | Schaefer et al. |
| 4,300,474 A | 11/1981 | Livsey |
| 4,323,756 A | 4/1982 | Brown et al. |

(Continued)

FOREIGN PATENT DOCUMENTS

WO    WO 03094774 A1 * 11/2003

*Primary Examiner* — Timothy H Meeks
*Assistant Examiner* — Cachet I Sellman
(74) *Attorney, Agent, or Firm* — Peter K. Johnson; James L. Larson; Barbara Daniels

(57) ABSTRACT

A method is provided for depositing a hard wear resistant surface onto a porous or non-porous base material of a medical implant. The wear resistant surface of the medical implant device may be formed by a Laser Based Metal Deposition (LBMD) method such as Laser Engineered Net Shaping (LENS). The wear resistant surface may include a blend of multiple different biocompatible materials. Further, functionally graded layers of biocompatible materials may be used to form the wear resistant surface. Usage of a porous material for the base may promote bone ingrowth to allow the implant to fuse strongly with the bone of a host patient. The hard wear resistant surface provides device longevity, particularly when applied to bearing surfaces such as artificial joint bearing surfaces or a dental implant bearing surfaces. An antimicrobial material such as silver may be deposited in combination with a metal to form an antimicrobial surface deposit.

48 Claims, 21 Drawing Sheets

U.S. PATENT DOCUMENTS

| | | | |
|---|---|---|---|
| 4,367,017 A | 1/1983 | Jimbou et al. | |
| 4,434,189 A | 2/1984 | Zaplatynsky | |
| 4,537,793 A | 8/1985 | Kehrer et al. | |
| 4,568,565 A | 2/1986 | Gupta et al. | |
| 4,603,257 A | 7/1986 | Packer et al. | |
| 4,615,903 A | 10/1986 | Miller | |
| 4,644,127 A | 2/1987 | La Rocca | |
| 4,677,274 A | 6/1987 | Bisiach | |
| 4,681,640 A | 7/1987 | Stanley | |
| 4,701,592 A | 10/1987 | Cheung | |
| 4,724,299 A | 2/1988 | Hammeke | |
| 4,732,778 A | 3/1988 | Kawasaki | |
| 4,804,815 A | 2/1989 | Everett | |
| 4,818,562 A | 4/1989 | Arcella et al. | |
| 4,832,982 A | 5/1989 | Mori et al. | |
| 4,853,250 A | 8/1989 | Boulos et al. | |
| 4,863,538 A | 9/1989 | Deckard | |
| 4,927,992 A | 5/1990 | Whitlow et al. | |
| 4,938,816 A | 7/1990 | Beaman et al. | |
| 4,944,817 A | 7/1990 | Bourell et al. | |
| 4,947,463 A | 8/1990 | Matsuda et al. | |
| 4,976,930 A | 12/1990 | Kishida et al. | |
| 5,017,753 A | 5/1991 | Deckard | |
| 5,038,014 A | 8/1991 | Pratt et al. | |
| 5,043,548 A | 8/1991 | Whitney et al. | |
| 5,111,021 A | 5/1992 | Jolys et al. | |
| 5,132,143 A | 7/1992 | Deckard | |
| 5,147,680 A | 9/1992 | Slysh | |
| 5,155,324 A | 10/1992 | Deckard | |
| 5,156,697 A | 10/1992 | Bourell et al. | |
| 5,182,170 A | 1/1993 | Marcus et al. | |
| 5,182,430 A | 1/1993 | Lagain | |
| 5,208,431 A | 5/1993 | Uchiyama et al. | |
| 5,245,155 A | 9/1993 | Pratt et al. | |
| 5,252,264 A | 10/1993 | Forderhase et al. | |
| 5,272,312 A | 12/1993 | Jurca | |
| 5,285,046 A | 2/1994 | Hansz | |
| 5,290,368 A | 3/1994 | Gavigan et al. | |
| 5,308,661 A | 5/1994 | Feng et al. | |
| 5,314,003 A | 5/1994 | Mackay | |
| 5,316,580 A | 5/1994 | Deckard | |
| 5,368,947 A | 11/1994 | Denney | |
| 5,384,523 A | 1/1995 | Masuda | |
| 5,385,780 A | 1/1995 | Lee | |
| 5,393,613 A | 2/1995 | MacKay | |
| 5,393,957 A | 2/1995 | Misawa et al. | |
| 5,398,193 A | 3/1995 | Misawa et al. | |
| 5,413,641 A | 5/1995 | Coulon | |
| 5,418,350 A | 5/1995 | Freneaux et al. | |
| 5,431,967 A | 7/1995 | Manthiram et al. | |
| 5,434,880 A | 7/1995 | Burrows et al. | |
| 5,449,536 A | 9/1995 | Funkhouser et al. | |
| 5,453,329 A | 9/1995 | Everett et al. | |
| 5,471,541 A | 11/1995 | Burtnyk et al. | |
| 5,477,026 A | 12/1995 | Buongiorno | |
| 5,478,983 A | 12/1995 | Rancourt | |
| 5,484,980 A | 1/1996 | Pratt et al. | |
| 5,512,162 A | 4/1996 | Sachs et al. | |
| 5,530,221 A | 6/1996 | Benda et al. | |
| 5,578,227 A | 11/1996 | Rabinovich | |
| 5,607,730 A | 3/1997 | Ranalli | |
| 5,612,099 A | 3/1997 | Thaler | |
| 5,620,552 A | 4/1997 | Denney | |
| 5,640,667 A | 6/1997 | Freitag et al. | |
| 5,647,931 A | 7/1997 | Retallick et al. | |
| 5,688,564 A | 11/1997 | Coddet et al. | |
| 5,697,043 A | 12/1997 | Baskaran et al. | |
| 5,786,023 A | 7/1998 | Maxwell et al. | |
| 5,824,045 A * | 10/1998 | Alt | 623/1.15 |
| 5,837,960 A | 11/1998 | Lewis et al. | |
| 5,843,186 A * | 12/1998 | Christ | 623/6.56 |
| 5,961,858 A | 10/1999 | Britnell | |
| 5,984,905 A * | 11/1999 | Dearnaley | 604/265 |
| 5,985,056 A | 11/1999 | McCay et al. | |
| 5,993,550 A | 11/1999 | Eloy | |
| 5,993,554 A | 11/1999 | Keicher et al. | |
| 6,046,426 A | 4/2000 | Jeantette et al. | |
| 6,122,564 A | 9/2000 | Koch et al. | |
| 6,203,861 B1 | 3/2001 | Kar et al. | |
| 6,268,584 B1 | 7/2001 | Keicher et al. | |
| 6,306,467 B1 | 10/2001 | White et al. | |
| 6,316,744 B1 | 11/2001 | Nowotny et al. | |
| 6,344,246 B1 | 2/2002 | Fischer et al. | |
| 6,428,579 B1 * | 8/2002 | Valentini | 623/23.76 |
| 6,429,402 B1 | 8/2002 | Dixon et al. | |
| 6,476,343 B2 | 11/2002 | Keicher et al. | |
| 6,504,127 B1 | 1/2003 | McGregor et al. | |
| 6,520,996 B1 | 2/2003 | Manasas | |
| 6,526,327 B2 | 2/2003 | Kar et al. | |
| 6,534,745 B1 | 3/2003 | Lowney | |
| 6,548,125 B2 | 4/2003 | Warnecke | |
| 6,565,913 B2 * | 5/2003 | Arps et al. | 427/2.24 |
| 6,656,409 B1 | 12/2003 | Keicher et al. | |
| 6,703,038 B1 | 3/2004 | Kiefer et al. | |
| 6,717,106 B2 | 4/2004 | Nagano et al. | |
| 7,001,672 B2 * | 2/2006 | Justin et al. | 428/615 |
| 2002/0008274 A1 | 1/2002 | Nakagawa | |
| 2004/0191106 A1 * | 9/2004 | O'Neill et al. | 419/2 |
| 2004/0243241 A1 | 12/2004 | Jstephanous et al. | |
| 2005/0197689 A1 * | 9/2005 | Molaei | 623/1.13 |
| 2005/0220837 A1 * | 10/2005 | Disegi et al. | 424/423 |

\* cited by examiner

Direction of Movement of Part

Direction of Movement of Part

Direction of Movement of Part

LASER BASED METAL DEPOSITION (LBMD) OF ANTIMICROBIALS TO IMPLANT SURFACES

CROSS-REFERENCE TO RELATED DOCUMENTS

This application claims the benefit of:

Pending prior U.S. Provisional Patent Application No. 60/811,934, filed Jun. 7, 2006 by Brent E. Stucker, et al. for INCORPORATION OF SILVER INTO MATERIALS DEPOSITED BY LBMD, which is incorporated herein by reference.

The following are also incorporated herein by reference:

Pending prior U.S. patent application Ser. No. 11/432,426, filed May 10, 2006 by Daniel F. Justin et al. for LASER BASED METAL DEPOSITION (LBMD) OF IMPLANT STRUCTURES;

Pending prior U.S. patent application Ser. No. 11/253,850 filed Oct. 18, 2005 by Daniel F. Justin et al. for LASER BASED METRAL DEPOSITION OF IMPLANT STRUCTURES;

Issued U.S. patent application Ser. No. 10/811,038, filed Mar. 26, 2004 by Daniel F. Justin et al. for LASER ENGINEERED NET SHAPING OF IMPLANT STRUCTURES, issued as U.S. Pat. No. 7,001,672 on Feb. 21, 2006; and Prior U.S. Provisional Patent Application No. 60/527,118, filed Dec. 3, 2003 by Daniel F. Justin et al. for LASER ENGINEERED NET SHAPING OF IMPLANT STRUCTURES.

FIELD OF THE INVENTION

The present invention relates to the formation of biocompatible materials onto a medical implant device, and more particularly to the use of laser based metal deposition of biocompatible materials onto base implant material structures.

BACKGROUND OF THE INVENTION

The advancement of enhanced materials for the use of medical implants, such as joint prostheses has immensely improved the quality of life for many people over the past century. Devices such as artificial hips, knees, shoulders and other devices have allowed people who would otherwise have suffered from chronic pain and physical limitation to live active, comfortable lives. The development of such devices has confronted scientists and engineers with many technical challenges, such as in the area of materials science engineering wherein to achieve optimal implant performance various biocompatible materials with different physical and mechanical properties are bonded to each other.

Materials used for such devices must not only be non-corrosive, but must also be sufficiently resilient (having high tensile and compressive strength), and hard (having sufficient wear resistance). Since a device such as an artificial joint must undergo a great number of cycles of wear during the lifetime of the host patient, such devices must also possess great fatigue properties.

Some medical implant devices such as artificial joints must bond in some way with the patient's natural bone. Early devices employed bonding polymers, commonly referred to as bone cement to bond the implant rigidly to the anatomic structure of bone. However, more recently such devices have been constructed of porous materials such as porous Titanium (Ti) and porous Tantalum (Ta). The bone of the host patient grows into the porous material creating a strong permanent mechanical bond without the use of bone cements. Consequently, such implants are more reliable and durable in the long term than those relying on bone cement for fixation.

Such implant devices are typically manufactured from a wrought alloy, forged alloy or a powder metal injection molded process. While this produces an implant device with bulk properties that are optimized for certain overall design criteria such as biocompatibility strength and modulus of elasticity, these properties may not be optimized for property requirements specific to certain portions of the implant, such as wear or bone ingrowth characteristics.

For instance, while the use of porous materials such as porous Ti provides crucial and beneficial bonding properties, such materials may not have optimal properties in other areas. For example, porous materials may not be as hard as some other biocompatible materials and therefore may not have acceptable wear properties. However, because of the overriding importance of strong permanent bonding with the host patient bone, such porous materials have continued to be used in spite of less than optimal wear properties.

In order to enhance the wear properties of a device such as an artificial joint, prior art devices have been constructed in more than one piece. A first portion of the joint implant, that which will bond to the bone, has typically been constructed of a porous material such as porous titanium, and a second piece, such as the bearing surface of the joint has been constructed of a much harder, more wear resistant material such as alloys of cobalt and chrome (Co—Cr). The first and second pieces are then bonded together in an attempt to obtain the benefits of both materials. One challenge to using such a technique is that of achieving a sufficiently strong, permanent bond between the first and second portions, without the use of adhesives that may be biologically incompatible or may fail under the stresses imposed by the body of the patient. Attempting to weld such materials together can cause the non-porous material to flow into the porous material, destroying the porosity of the porous material and degrading the ability of the device to bond with the patient's bone. In addition, such materials, being dissimilar metals, often experience galvanic corrosion when bonded together in such a manner.

Therefore, there remains need for a device (and method for making the same) such as an artificial joint which can take advantage of the properties of a first material, such as the porosity of porous Ta or Ti, and also take advantage of the properties of a second material, such as the hardness of a material like Co—Cr, for use in a bearing environment such as a ball or socket of a joint. Such a device would preferably not exhibit any delamination between the two materials and would not experience any galvanic corrosion. Such a device would also preferably not diminish the porosity of the porous material due to the flow of the other material thereinto.

SUMMARY OF INVENTION

The present invention provides a method for constructing a medical implant such as a hip prosthesis, having a bulk portion constructed of a porous material which can fuse with a host patient's bone structure, and which also has a hard, wear resistant material only at portions of the device where such properties are desired. According to the invention, a laser based metal deposition (LBMD) layer of relatively dense hard material, can be applied to a porous material base structure or a non-porous material base structure.

The relatively hard, wear resistant biocompatible material can be for example an alloy of cobalt and chrome alloy, whereas the porous material could be a biocompatible material conducive to bony tissue ingrowth when formed in a porous structure such as porous Titanium, Ti6Al4V, Ti6Al4V ELI, Titanium-Nickel alloys, Tantalum, Tantalum alloys, and porous structures made from other materials that have an exposed surface made from biocompatible materials. Some applications may call for a non-porous base material, in which case suitable base materials include Titanium, Ti6Al4V, Ti6Al4V ELI, Titanium-Nickel alloys, Niobium, Zirconium, Tantalum, stainless steels and alloys related to these metals. In these applications, the relatively hard wear resistant biocompatible material can comprise of materials such as carbides, oxides, nitrides or other compositions that are harder or more wear resistant than the non-porous biocompatible base materials.

According to the LBMD material application of the present invention, the applied material can be applied as, for example, powdered metal, as a wire or as a foil. The applied material is then melted by a high-energy laser immediately upon or soon after application. The use of a laser to heat the applied material advantageously allows the heating to be very localized, thereby minimizing any adverse effects of such heat on the underlying material. However, in this invention, other sources of energy such as plasma and electron beam energy could also be focused and localized to allow energy based metal deposition of material through similar processes. Thus, in this invention laser energy is the preferred energy source. However it is understood that the term Laser Based Metal Deposition (LBMD) is meant to include any other energy source that can provide sufficient energy locally to melt and deposit the additive material, but minimize any adverse effects of such heat on the underlying base material.

In addition, the extremely localized heating of the laser, or any other localized energy source, in conjunction with the heat sinking properties of the underlying material leads to very rapid subsequent cooling, resulting in a beneficial small grain structure as well as allows the addition of carbon interspersions when conducted in a carbon-rich environment or with powdered or alloyed carbon added to the deposition material, both of which provide increased hardness to the deposited material.

Furthermore, since the LBMD deposited material is heated and cooled so quickly and locally, the applied material tends not to flow excessively into the porous or underlying non-porous base material, thereby maintaining the desirable porous properties of the porous bulk portion of the device or preferred mechanical and physical properties of the non-porous base material. This also creates a relatively small bonding zone between the base material and the LBMD deposited material. This allows for a thin layer of LBMD deposited material to be deposited onto the base material. Because this layer of deposited material is thin, implants can be fabricated that are optimized in size to limit the amount of bone that must be removed to facilitate the bulk of the implant. For example, a 5 millimeter thick sheet-like implant with a 3 millimeter thick porous bone ingrowth underside, a 0.5 millimeter bonding zone, and 1.5 millimeter bearing surface made from a first layer of Titanium and a second layer of Cobalt-Chrome can be placed as bearing pads on the proximal tibial plateau as a tibial hemiplasty implant in the knee. This construct of the 5 millimeter thick implant is significantly bone conserving compared to traditional 9 millimeter to 20 millimeter thick tibial implants that are currently used to resurface the proximal tibia of the knee.

In another aspect of the invention, a relatively hard material such as Co—Cr can be applied to the surface of a porous base such as porous Tantalum, and the Co—Cr surface used to bond to a Co—Cr bulk portion of the device. This overcomes the problems that have previously been experienced, when trying to bond a material such as Co—Cr to another material such as porous Tantalum. A corrosion barrier, such as a layer of Ti may be provided between the porous Tantalum and the Co—Cr.

Another aspect of the invention it that the invention allows for more economical fabrication of implantable devices. For example, the manufacturing process can be optimized utilizing aspects of this invention by making the base structure from a readily manufacturable material and depositing a second material on to the base material using LBMD. Biocompatible materials with inherently greater hardness and more difficult machinability characteristics, such as Titanium Carbide, can be selectively deposited onto more easily machinable materials such as a wrought Titanium alloys. This allows for the majority of the implant made from the more easily machinable wrought alloy to be fabricated into the base shape of the implant. Then, only the articulating bearing surfaces of the implant need to be fabricated from the LBMD deposited harder material such as titanium carbide (TiC). In this example, titanium carbide is used as the harder LBMD material. However, any articulating bearing material may be deposited on any more easily machined base material as long as the specific metallurgic chemistry between the two materials allows for bonding between the two materials without the excessive addition of tertiary phases of interstitial materials that prevent adequate bonding.

The present invention can also allow use of a blended composite coating in order to enhance the coating performance. This approach allows one to tailor the coating properties as desired by choosing a suitable matrix and reinforcing phases. The matrix material, such as Titanium, addresses the considerations of metallurgical compatibility, metallurgical bonding and coating brittleness, while the reinforcing second phase material, such as Titanium Carbide, takes care of the hardness and wear resistance issues. In addition, the invention incorporates the principles of functionally graded materials, either to achieve desired property gradation across the coating thickness or to facilitate satisfactory coating deposition or both. Functionally graded materials (FGMs) are composite materials where the composition or the microstructure are locally varied so that a certain variation of the local material properties is achieved. This is achieved by closely controlling the amount and distribution of second phase particles across the coating thickness. The current approach helps achieve superior coating properties as well as minimize cracking problems during coating deposition.

The invention takes advantage of the capabilities of advanced direct metal deposition techniques, specifically, deposition of a composite coating using a laser based metal deposition process. Some of the advantages of this method include: i) the coating can be metallurgically bonded to the substrate, ii) minimal heat input and very narrow heat affected zones, iii) spatial variation in coating microstructure and properties is possible, iv) coating microstructure can be closely controlled, v) reduced residual stresses and distortion problems, and vi) precise control over coating application area. These capabilities are not available with conventional coating processes.

The invention produces coatings which are significantly thicker than most existing coating techniques. Existing techniques such as ion implantation or surface treatments of Titanium nitride or Titanium oxide produce surface treatments with thicknesses measured at the molecular or nanoparticle level, whereas the invention produces a coating thick enough to create a functional bearing surface. Compared to the relatively thin surface treatments described above, the LBMD thickness generally ranges from a fraction of a millimeter to multiple millimeters in thickness. The thickness of the coating is important, in that concentrated stresses at the surface of a thin coating result in concentrated stresses at the coating/substrate interface, which can lead to delamination. In addition, a certain amount of wear is expected when two materials are articulating against each other. In the case of the relatively thin existing surface treatment techniques, these materials wear away from the surface causing the softer underlying base material to be exposed. In contrast, load is transmitted through thicker coatings, the concentrated load at the surface passes through a larger volume of coating, and becomes distributed over a larger area as the stress reaches the coating/substrate interface, resulting in a lower concentration of stresses at the location of greatest failure potential.

The present invention provides a manufacturing method for producing an implant made from traditional or novel implant metals with layers of material having differing densities and structures.

The present invention provides a surface material deposition process that allows for a gradient of materials with varying selective properties to be deposited on the bulk implant material. After the base structure is formed, additional material is added to the base structure using the LBMD process.

The implant is formed in the approximate final shape from a common or novel orthopedic alloy such as Co—Cr alloys, titanium alloys, stainless steel alloys, or base pure metal such as tantalum, titanium or platinum. Because the basic structure of the implant is formed by conventional manufacturing means out of implant grade materials, the majority of the cost of the manufacturing is similar to existing implants.

Applicable implant shapes that can benefit from LBMD deposition of harder materials onto the base material include knee, shoulder, hip, finger, spine, top, foot, elbow, wrist, dental, jaw, and ankle prosthesis, just to name a few.

Besides improving bearing properties of implants, the LBMD process can be used to increase the bone ingrowth properties of implant surfaces. This can be done by either depositing a hard material onto a porous base material or depositing a porous material onto a hard material.

In the case of adding a hard material to a base material, a monoblock of a porous structure of an implant material is the base material. A closely packed fine grain structure of an implant material is then added to the base material by LBMD methods. The closely packed grain structure would result in improved wear properties.

The majority of the bulk of the implant can be manufactured by conventional methods. The hardened surface may then be added by LBMD deposition. Unlike structures that are completely made by methods such as LBMD, this method would allow the majority of the structure to be built by conventional methods with only thin layers of hard material added to the structure. Accordingly, cost savings can be achieved.

LBMD allows for a highly focused laser beam of energy to melt a very small amount of powder over a short period of time. Because the large bulk material acts as a heat sink, this process results in a rapidly cooled LBMD deposited material. Rapid cooling of materials such as metals results in a finer grain structure, which results in increased hardness. In addition, in a carbon rich environment, carbides form resulting in an even harder material. Since the hardness of a material is typically directly related to wear resistance, materials having high hardness become very attractive for use on bearing surfaces such as those on knee, hip, wrist and elbow joints as well as myriad other implant devices.

Using the material deposition process of the present invention, like materials can be deposited onto like materials such as Co—Cr alloys LBMD deposited on Co—Cr wrought materials. However, dissimilar materials may also be deposited, such as titanium alloys deposited on Co—Cr alloys, or Co—Cr alloys can be deposited on titanium and its alloys.

In selected embodiments of the present invention, materials having antimicrobial properties may be deposited on a metal base structure of an implant through the use of LBMD, with or without LENS techniques. Such materials may include, but are not limited to elemental silver, gold, platinum, palladium, iridium, copper, tin, antimony, bismuth, zinc, salts thereof, and intermetallics thereof. The antimicrobial material may be deposited along with other materials, such as a metal selected from cobalt-chrome, tantalum, titanium, platinum, zirconium, niobium, stainless steel, and alloys thereof. The deposit including the antimicrobial material may be formed as a single layer or as multiple layers, with or without functional gradients provided by variation in the proportions of the component materials deposited.

The systems and methods of the present invention may be used to provide a number of different types of implant surfaces, including bone apposition surfaces, articular surfaces, and surfaces that do not abut bone or articulate. Bone apposition surfaces may be deposited with a relatively high porosity to enhance bone in-growth. Articular surfaces may be formed with a higher hardness to provide enhanced wear resistance. A wide variety of implant surfaces, including those that do not articulate or contact bone, may desirably be formed with antimicrobial properties to reduce the probability of infection of the tissues surrounding the implantation site.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of this invention, as well as the preferred mode of use, reference should be made to the following detailed description read in conjunction with the accompanying drawings.

DETAILED DESCRIPTION OF THE PREFERRED EMBODIMENTS

The following description is the best embodiment presently contemplated for carrying out this invention. This description is made for the purpose of illustrating the general principles of this invention and is not meant to limit the inventive concepts claimed herein.

Figure 1:
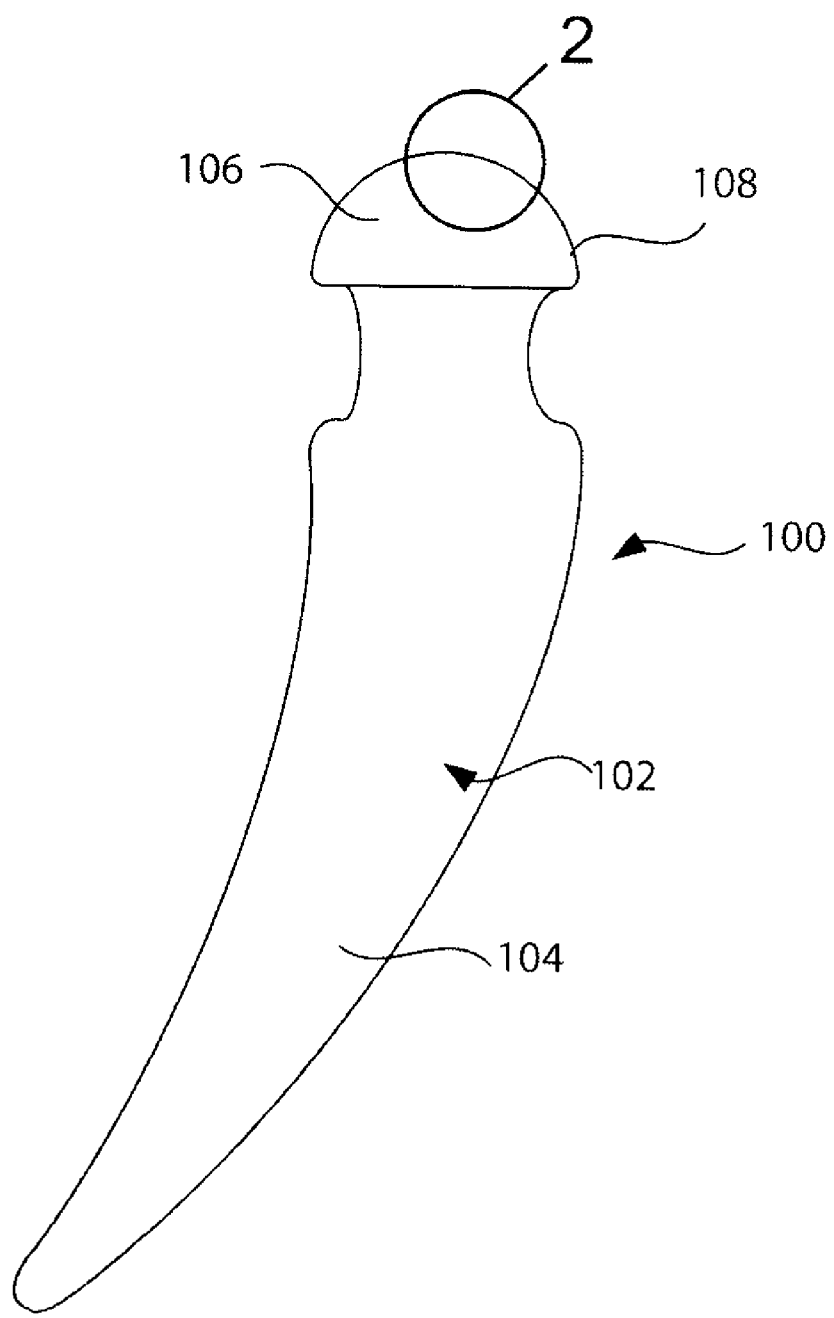
FIG. 1 shows an example of the present invention employed in a hip prosthesis.

With reference to FIG. 1, a preferred embodiment of the present invention will be described in terms of a hip prosthesis (hip) 100 for implanting in the body of a patient. However, this is only by way of example, and it should be understood the present invention can practiced on many other medically implanted devices, including without limitation, knee, shoulder and elbow prostheses, as well as many other devices. Note FIG. 5, discussed below.

The hip prostheses 100 must be constructed completely of biocompatible materials in order to ensure acceptance of the prostheses by the patient's body. A biocompatible material is one that will not cause an adverse reaction with a host patient, and that will not corrode when exposed to human tissue and fluids within the host patient. The hip 100 includes a base portion 102, which may include a shank 104 and a ball 106, and that is constructed predominantly or completely of a porous material such as porous Ti or Ta (or alloys thereof). Constructing the shank 104 of a porous material such as Ti or Ta advantageously promotes bone growth into the porous material and strong fusion therewith. This provides a strong, permanent, resilient bond with the bone of the host patient without the need for adhesives. As discussed above, the use of adhesives to bond the hip 100 to the bone of the host patient would not only provide a somewhat (unreliable bond, but could also lead to adverse reactions with the host patient.

As also mentioned above, the base 102 is constructed either completely or predominantly of a porous material, such as a porous matrix of Ta or Ta alloy, Ti or Ti alloy, for example Ti-6Al-4V, Ti—Ni, Ti6Al4V ELI, Titanium-Nickel alloys, and porous structures made from other materials that have an exposed surface made from biocompatible materials. The base 102 can be formed by methods such as casting, machining or forging.

A preferred material for the base 102 is porous tantalum. One such porous tantalum is sold under the brand name HEDROCEL® by IMPLEX® Corporation, 80 Commerce Drive, Allendale, N.J. 07401.

The preferred porous tantalum material such as HEDROCEL® has an open cell, tantalum metal structure that has the appearance of cancellous bone, and that can be formed or machined into complex shapes. It is distinguished from current porous materials by its uniformity and structural continuity as well as by its strength, toughness, and resistance to fatigue failure.

The tantalum metal structure consists of interconnecting pores, resulting in a construct that is >60% porous, and ideally >75% porous. In addition, the tantalum material preferably has flexural modulus properties that are similar to those of human bone. For articulating joint replacement devices, compression molded polyethylene can be infused into the tantalum structure, creating a bond as strong as the polyethylene itself. In addition, the titanium structure can be fabricated into products without the need for solid metal support.

The preferred porous tantalum metal (e.g., HEDROCEL®) has a similar cellular geometric appearance to bone graft, and also offers many beneficial attributes. The porous structure is preferably a uniform and homogeneous biomaterial, having load carrying capabilities that are engineered to the orthopedic application. Bone graft, whether harvested from the patient or taken from the bone bank, has varying, often unknown degrees of mechanical properties and overall quality. Similarly, the bone must incorporate into the surrounding bone for long-term clinical success. If the bone dies or does not generate new bone, the fatigue characteristics will be poor and can lead to collapse, loosening, pain, and re-operation. The preferred tantalum material is highly fatigue resistant and maintains its strength for the duration of clinical usage. The mechanical properties should not degrade with time. Since the stiffness properties of the preferred tantalum material are similar to bone, the load pattern to the surrounding bone should be maintained without a compromise of quality.

The preferred tantalum material has a volumetric porosity greater than traditional prosthetic materials and bone fixation surface coatings. This high porosity allows a more normal restoration of the bone in contact with the porous material, unlike the bone density change phenomenon seen with minimally porous or non-porous implant materials. The solid metals used in current implants are at least ten times stiffer than bone, whereas the tantalum material preferably has a stiffness similar to that of bone.

Initial stability is equally important and is necessary for proper bone in-growth. The tantalum material will preferably have high frictional characteristics when contacting bone. In the early post-operative period, these frictional and structural properties allow the implant device to remain very stable.

For soft tissue applications, the properties of porous tantalum have an important role. Similar to bone, the overwhelming volumetric porosity allows fast penetration of precursor cells and relatively fast formation of soft tissue fibral strands and blood supply. Unlike solid metal screws. washers or synthetic sutures, porous tantalum achieves the primary mode of tissue c attachment to the implant device while the tissues heal at their own variable pace. The struts of the porous tantalum material interlock with the tissue, offering immediate, secure and functional mechanical attachment. This allows for the necessary healing and reproducible tissue incorporation into the porous matrix. The use of a porous tantalum soft tissue anchoring device may therefore result in both soft tissue in-growth and bone in-growth for long-term fixation.

One method for forming a base 102 of porous tantalum is described in U.S. Pat. No. 5,282,861 to Kaplan, issued Feb. 1, 1994, and which is herein incorporated by reference. According to the method, the metal, such as tantalum, is deposited on a carbon foam substrate. A reaction chamber encloses a chlorination chamber and a hot wall furnace. A resistance heater surrounds the chlorination chamber and an induction heating coil surrounds the reaction chamber to heat the hot wall furnace. Tantalum metal is located within the chlorination chamber and a carbon foam substrate is positioned within the hot wall furnace. Chlorine gas is injected into the chlorination chamber to react with the tantalum to form tantalum chloride. The tantalum chloride mixes with hydrogen injected into the chamber and then passes through an opening in the hot wall furnace. The mixture is heated within the hot wall furnace of a temperature of approximately 1100° C. to produce the following reacting surface $TaCl_5 + 5/2H_2 \rightarrow Ta + 5\ HCl$. The surface reaction deposits the tantalum on the carbon foam substrate to produce a uniform thin film over the individual ligaments of the substrate. The hydrogen chloride is then exhausted.

It should be appreciated that although the substrate has been indicated to be carbon, other carboneous materials, such as graphite, may be used. In addition, other open cell materials, such as high temperature ceramics, may also be used. Also, other layers may be deposited on the substrate, such as intermediate layers to provide additional strength. Other aspects of the invention could be the incorporation of a core of solid material, such as tantalum or niobium or alloys of each, with the porous substrate fitted around the solid core and with the subsequent deposition of metal not only covering the substrate but also locking the porous substrate to the solid core.

The base 102 may also comprise porous tantalum formed on a substrate material. A method for forming the base 102 of porous tantalum on a substrate material is disclosed in U.S. Pat. No. 6,063,442 to Cohen et al, issued May 16, 2000, and which is herein incorporated by reference.

In another method of forming the base 102, spherical beads or particles (not shown) of Ti or Ti alloy can be charged into a mold or form. The beads are preferably of relatively uniform shape. It is within the skill of one in the art to select a bead size range to result in a desired porous matrix with the desired pore size. The beads can then be exposed to high temperature in a Hot Isostatic Pressing (HIP) process to sinter the beads into the desired solid matrix form.

The HIP process is carried out in an oven that includes an airlock. The base 102 is prepared as described above and placed within the oven, which is then evacuated and charged with an inert (e.g., argon) atmosphere. The oven is heated to the desired temperature while the atmosphere therein is pressurized to the desired pressure. The HIP process applies an isostatic pressure through the inert gas (e.g., argon). By applying sufficient pressure during the heating step, the beads are fused together at temperature below that which would adversely affect the microstructure of the material.

With continued reference to FIG. 1, the hip 100 also includes a ball 106 which has a relatively dense, hard and wear resistant outer surface region 108 due to the unique processing and material described hereinbelow. The ball 106 fits within a prosthetic acetabular socket cup (not shown) and the outer surface region 108 of the ball 106 forms a bearing surface with the inner surface of the socket cup. While the porous material, such as porous Ti or Ta making up the base 102 (and ball 106) has advantageous bone fusion properties, it would not have optimal wear properties for surfaces such as the bearing surface of the ball 106.

Figure 2:
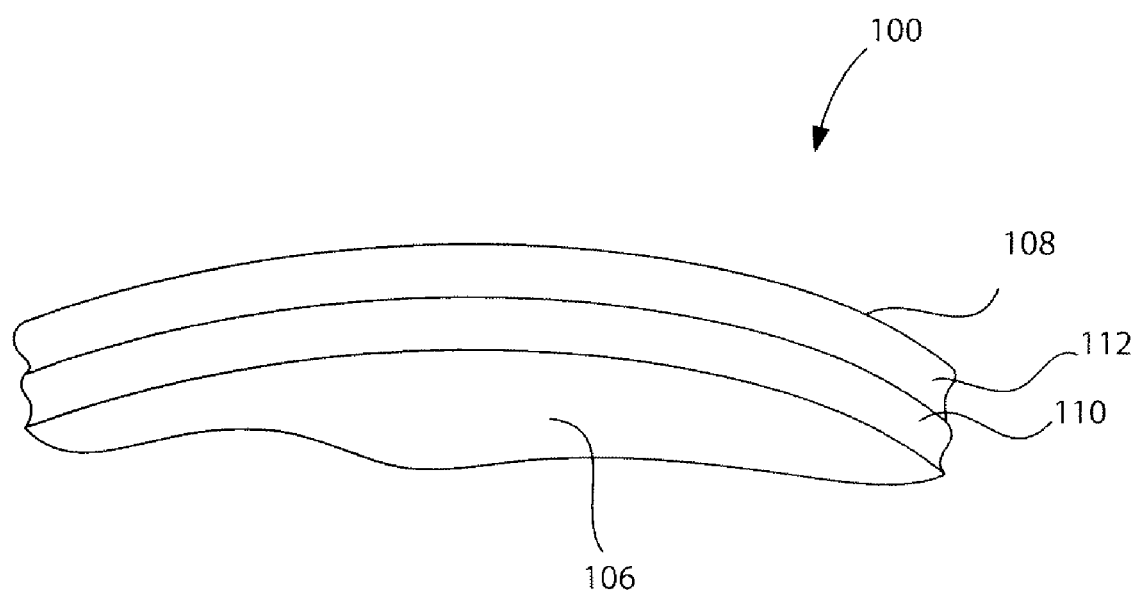
FIG. 2 is a view taken from circle 2 of FIG. 1, showing the a cross section of the surface of the hip prosthesis of FIG. 1.

With reference to FIG. 2, the outer surface region 108 of the ball 106 of the hip 100 can be seen in more detail. The outer surface region 108 includes a corrosion barrier layer 110 over which a hard dense outer material 112 such as Co—Cr is formed.

The outer surface region 108, including the corrosion barrier layer 10 and the outer material 112, can be constructed as laser based metal deposition (LBMD) layers. An example of a LBMD process is Laser Engineered Net Shaping (LENS™), Sandia Corporation of Albuquerque, N. Mex., is described in U.S. Pat. No. 6,046,426 to Jeantette, et al., issued on Apr. 4, 2000, and which is incorporated herein by reference. Initially, a layer is deposited directly on the ball 106. Thereafter, subsequent layers can be deposited on previous layers in a controlled manner until a desired surface shape is formed. The material can be deposited for example as a powdered metal emitted from one or more nozzles. Alternatively, the material could be provided as a wire or as a foil, held in proximity to the base and heated with the laser.

Figure 3A:
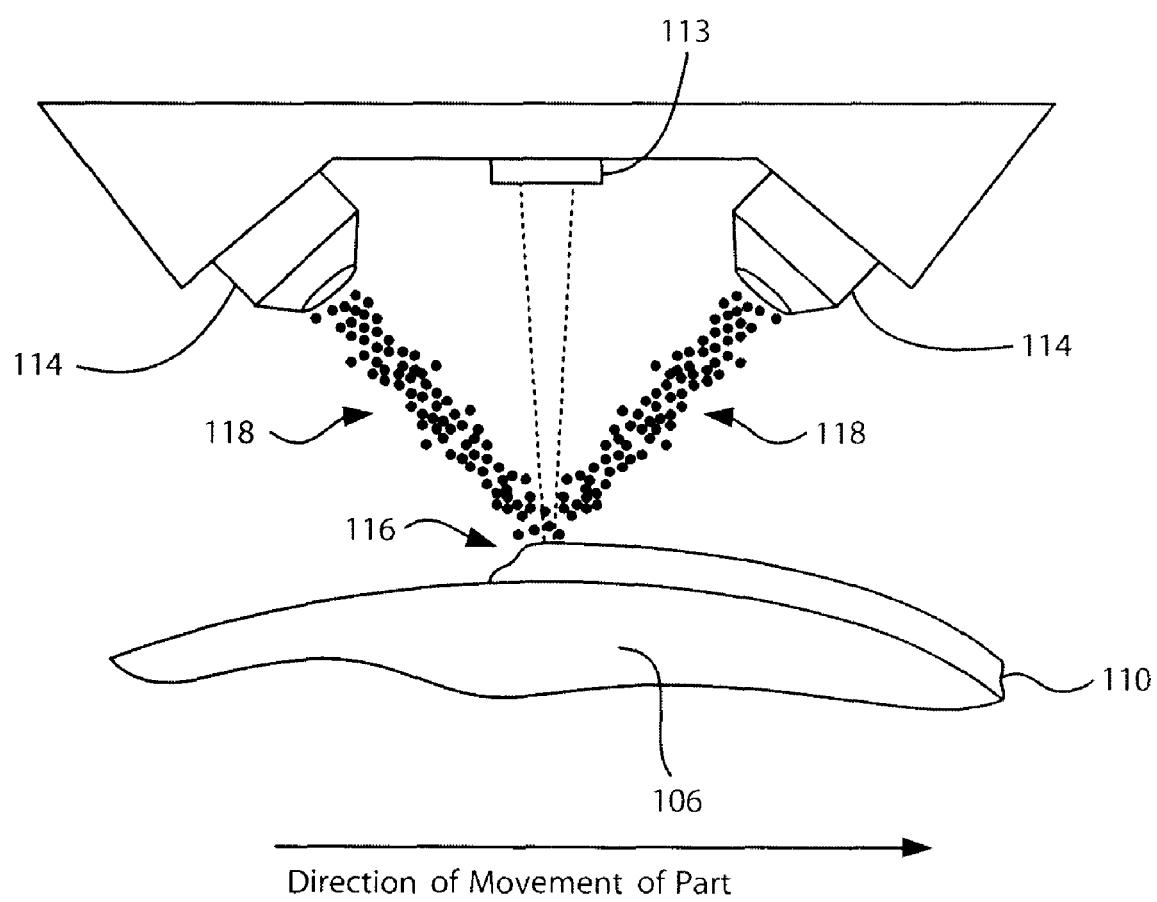
FIG. 3A illustrates the deposition of a first material using laser based metal deposition (LBMD)
Figure 3B:
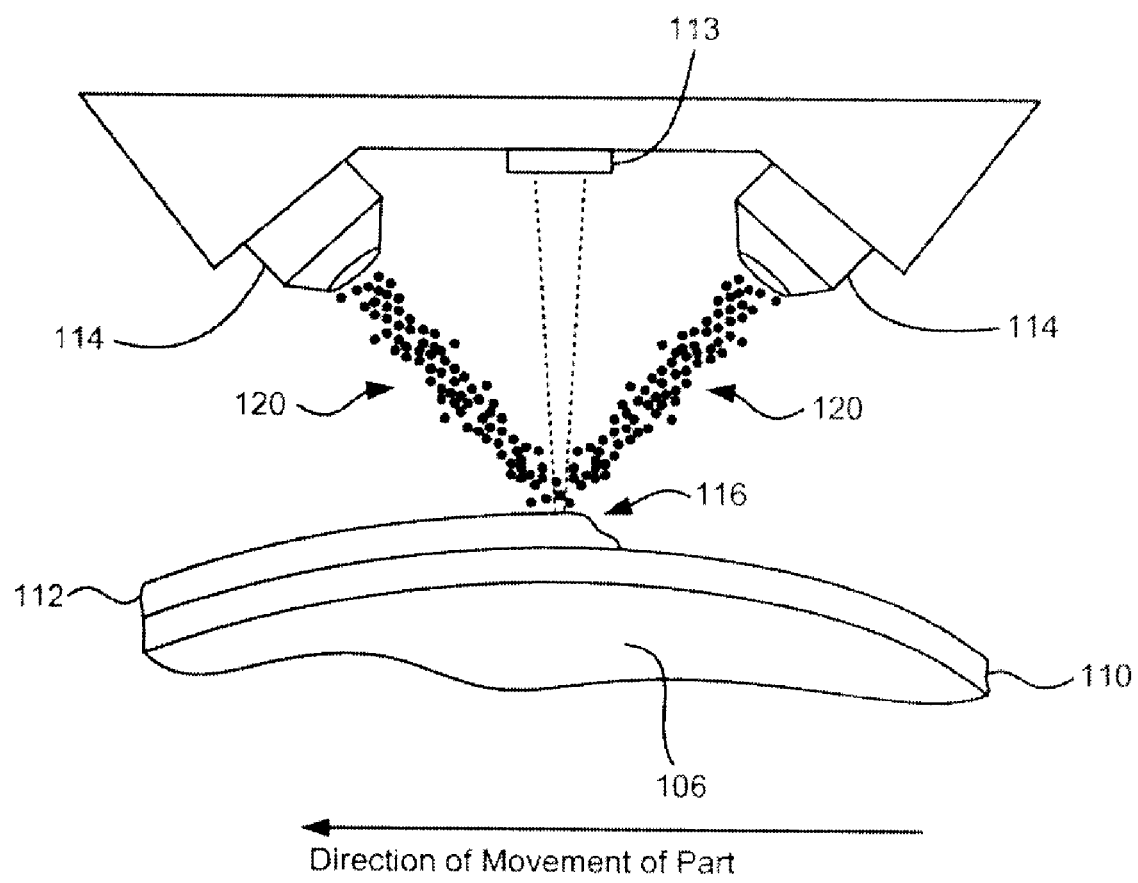
FIG. 3B illustrates the deposition of a second material on the first material of FIG. 3A using laser based metal deposition (LBMD)

FIGS. 3A-B illustrate the construction of the outer surface region 108 of the ball 106 according to a preferred LBMD process. As shown, the corrosion barrier layer 10 is formed first by depositing a layer of corrosion-resistant material 118 such as Ti or Ti alloy onto the ball 106, and immediately heating the material with a high power laser 113. Then the outer layer 112 is formed on the corrosion barrier layer 110, again by deposition and laser heating. More detail D about a preferred process is provided below.

As shown in FIG. 3A, a powdered material feeder (not shown) provides a uniform and continuous flow of a measured amount of powdered material 118 to the delivery system, or nozzle 114 The delivery system directs the powdered material 118 toward the ball 106 and directs the powdered material 118 to flow in a converging, conical pattern whereby the apex of such converging, conical pattern intersects the minimum diameter of a focused laser beam (i.e. focus or focal plane) produced by a laser 1113 such as an Nd YAG laser, all of which is in close proximity to the surface of the base 102. This generates a melt zone 116, wherein a substantial portion of the powdered material 118 melts and is deposited on the surface of the ball 106. Those skilled in the art will appreciate that such powdered material can melt either in flight or upon injection into a molten puddle of powdered material. By causing the ball 106 to move relative to the delivery system or by moving the delivery system relative to the ball 106, layers of molten deposited material can be deposited to form a net-shaped surface.

The deposited corrosion barrier layer 10 may be deposited as a single layer, or as multiple layers applied by successive passes of LBMD deposition. For instance, laminates of corrosion-resistant material (e.g., Ti and/or Ti alloys, etc.) can be formed to create the corrosion barrier layer 110.

Figure 3C:
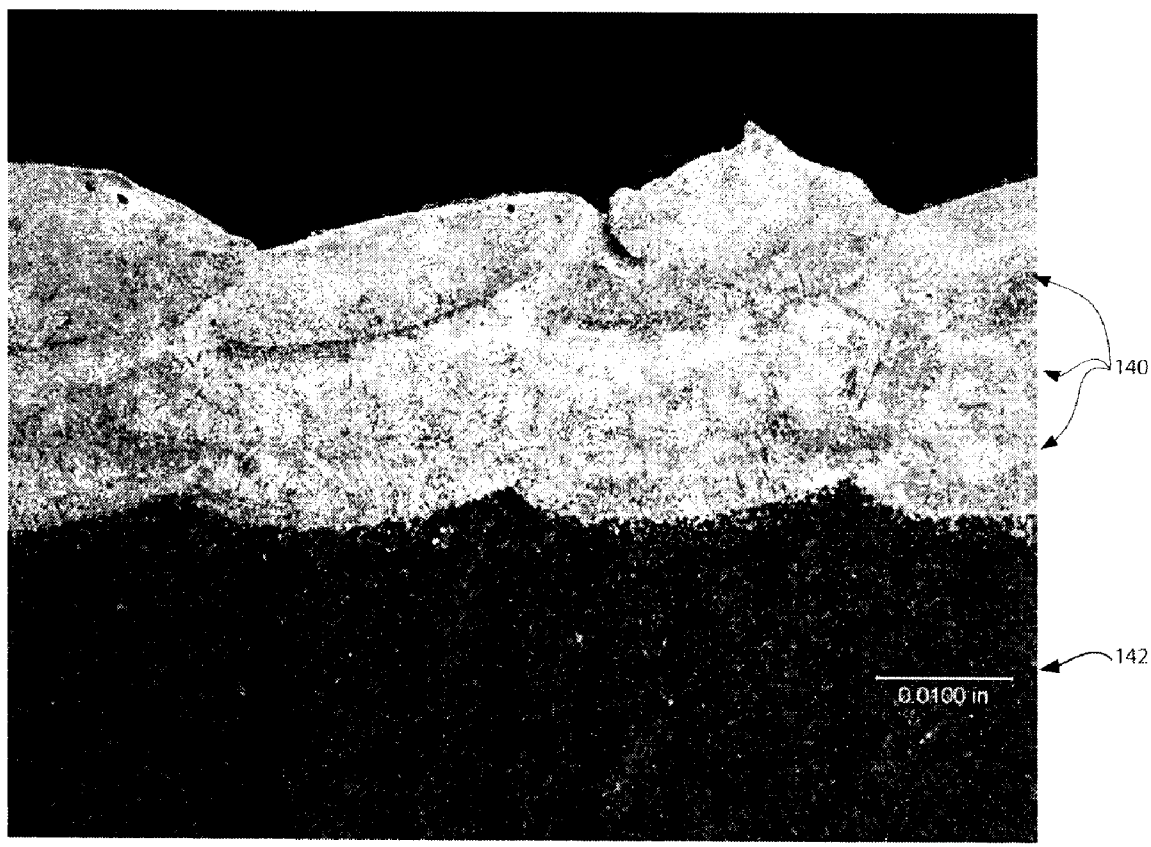
FIG. 3C is a micrograph at 5× magnification that shows three layers of Co—Cr alloy deposited by the LBMD process on a bulk material of wrought Co—Cr.
Figure 3D:
FIG. 3D is a micrograph at 5× magnification of nine layers of Co—Cr alloy deposited by LBMD on a bulk material of wrought Co—Cr.
Figure 3E:
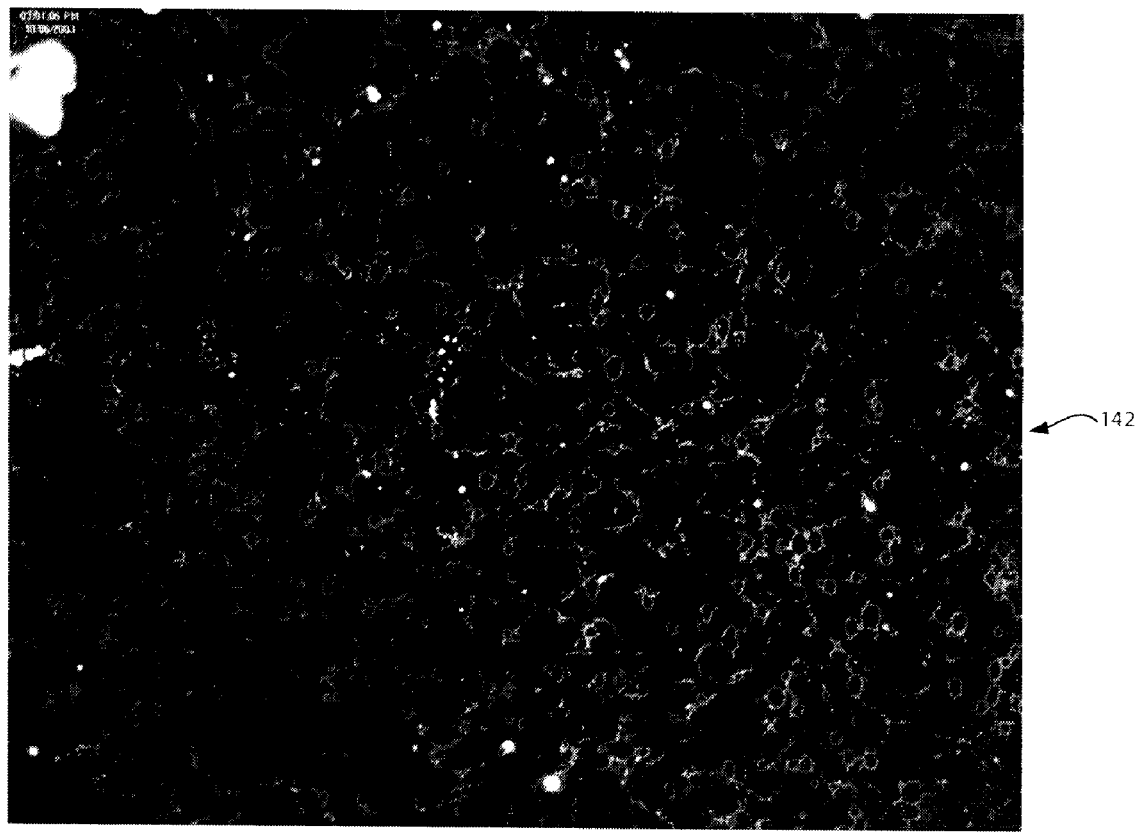
FIG. 3E is a micrograph at 50× magnification showing the bulk wrought Co—Cr alloy.
Figure 3F:
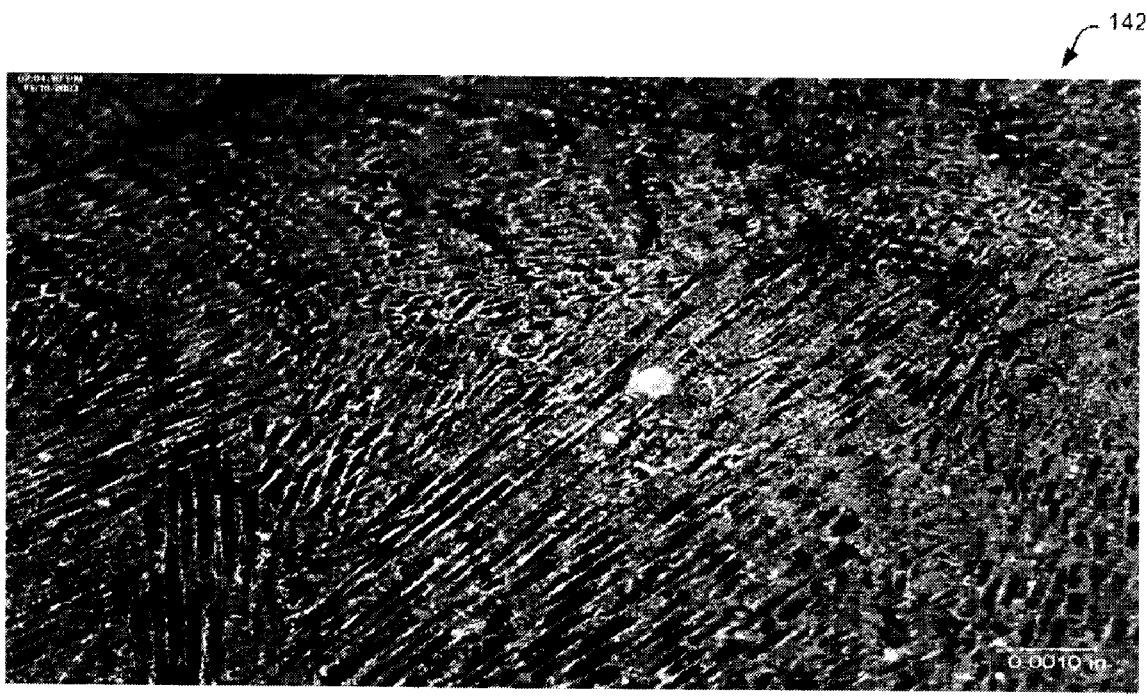
FIG. 3F is a micrograph at 50× magnification showing the LBMD deposited Co—Cr alloy, particularly showing the finer grain structure associated with a rapidly cooled LBMD deposited material.

Referring to FIG. 3B, the layer of outer material 112 is formed on the corrosion barrier layer 110 by a LBMD process as set forth above, this time using biocompatible material 120 that has a high wear resistance, such as Co—Cr alloy. Again, laminates of high wear resistance material can be formed. FIG. 3C is a micrograph at 5× magnification that shows three layers of Co—Cr alloy 140 deposited by the LBMD process on a bulk material of wrought Co—Cr 142. FIG. 3D is a micrograph at 5× magnification of nine layers of Co—Cr alloy deposited by LBMD on a bulk material of wrought Co—Cr. FIG. 3E is a micrograph at 50× magnification showing the bulk wrought Co—Cr alloy. FIG. 3F is a micrograph at 50× magnification showing the LBMD deposited Co—Cr alloy, particularly showing the finer grain structure associated with a rapidly cooled LBMD deposited material.

Either of the layers 110, 112 can also be formed to have a gradient of material qualities; for example the outer material 112 could be formed to become progressively harder toward the outer surface of the outer material 112.

Additional layers can also be added above, below, or between the corrosion barrier layer 110 and layer of outer material 112 per the desires of the manufacturer or need in the industry.

The LBMD deposition process is preferably performed in a controlled atmosphere chamber (not shown) which contains an inert gas to inhibit the formation of surface oxide in the deposition area. This reduces the amount of laser energy needed to achieve full melting of the powder. Although deposition can be performed outside the controlled atmosphere chamber, the inert atmosphere will promote full density in the deposited structure and ultimately lead to improved strength of the applied surface material.

It should be appreciated that the laser heats the LBMD deposited material in a very localized manner and for a very short duration. Because of this the heat does not appreciably heat the base material, and thus the heat does not adversely affect the structure of the base material. Furthermore, the large heat sink of the ball 106 combined with the very small area of localized heating causes the heated deposited material to very rapidly cool. This results in a finer grain structure than would occur with a slower cooling, and also results in carbide interspersions when conducted in a carbon-rich environment. As those skilled in the art will appreciate, fine grain structure and the presence of carbide interspersions both contribute to improved hardness and therefore improved wear properties.

In addition, because of the rapid rate of heating and cooling, the applied material does not tend to excessively flow into porous material, thereby maintaining the desirable porous properties of the porous bulk portion of the device and a relatively small bonding zone between the porous material and the LBMD deposited material. This allows for a thin layer of LBMD deposited material to be deposited onto porous material. Because this layer of deposited material is thin, implants can be fabricated that are optimized in size to limit the amount of bone that must be removed to facilitate the bulk of the implant. For example, a 5 millimeter thick sheet-like implant with a 3 millimeter thick porous bone ingrowth underside, a 0.5 millimeter bonding zone, and 1.5 millimeter bearing surface made from a first layer of Titanium and a second layer of Cobalt-Chrome can be placed as bearing pads on the proximal tibial plateau as a tibial hemiplasty implant in the knee. This construct of the 5 millimeter thick implant is significantly bone-conserving compared to traditional 9 millimeter to 20 millimeter thick tibial implants that are currently used to resurface the proximal tibia of the knee.

As mentioned above, the deposited layers may be deposited as multiple layers applied by successive passes of LBMD deposition. It should be pointed out the heat used to apply each layer and/or the material composition can be adjusted with each pass to achieve a gradient of material properties if desired. For example, the layer could be applied so that the applied layers are progressively harder toward the surface of the structure.

Another preferred embodiment includes a multi-layer "sandwich" of Co—Cr alloy (outer material 112) on titanium (corrosion barrier layer 110) on a porous tantalum or titanium base material. LBMD is used to directly deposit titanium onto porous tantalum or titanium and Co—Cr onto the previously deposited titanium. Illustrative dimensions of such an embodiment follow. The thickness of the porous tantalum can be about 0.040 to 1.000 inches, the thickness of the mixed titanium and tantalum layer can be between about 0.010 and 0.050 inch. The thickness of the titanium layer can be between about 0.010 and 0.050 inch. The thickness of the mixed titanium and Co—Cr layer can be about 0.001 to 0.010 inch. The thickness of the Co—Cr layer can be about 0.010 to 0.500 inch. Thus, a sandwich of tantalum, titanium, Co—Cr could range from about 0.071 inches to 1.61 inches. Of course these dimensions are provided by way of example, and will vary depending on the type and use of the implant device.

Figure 10:
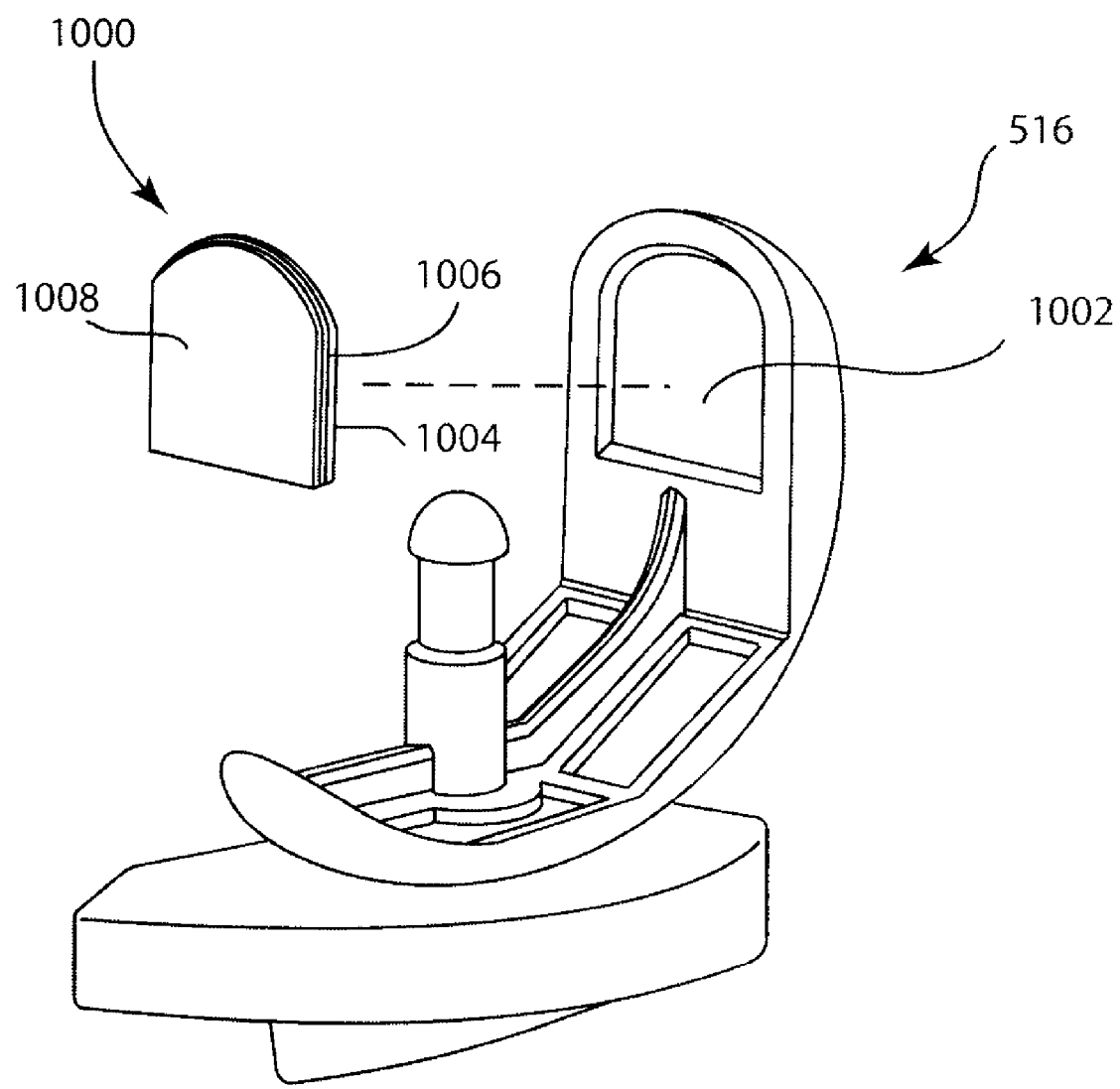
FIG. 10 is an exploded view the knee implant of FIG. 5 and a multi-layer structure coupling thereto.

According to another preferred embodiment, multi-layer structures such as that described in the preceding paragraph can be formed for coupling to another device such as a commercially available implant. For instance, such multi-layer structures can be fusion or diffusion bonded to implants that are made by traditional methods. Thus, for example, the Co—Cr surface of a 0.200 inch three layer structure could be diffusion bonded to a hip or knee implant, as shown in FIG. 10. The porous surface would then advantageously be available for coupling to bone of a host patient.

In fusion bonding, the substrates are first forced into intimate contact by applying a high contact force. The substrates are then placed in a furnace and annealed at high temperature, after which a solid bond is formed between the substrates. In diffusion bonding, the substrates are forced into intimate contact under high contact force, and heated at a temperature below the melting point of the substrate materials. Fusion bonds involve the complete melting and mixing of both metals. Diffusion bonding can be viewed as a form of fusion bonding but with much less melting and mixing of both metals.

Figure 4:
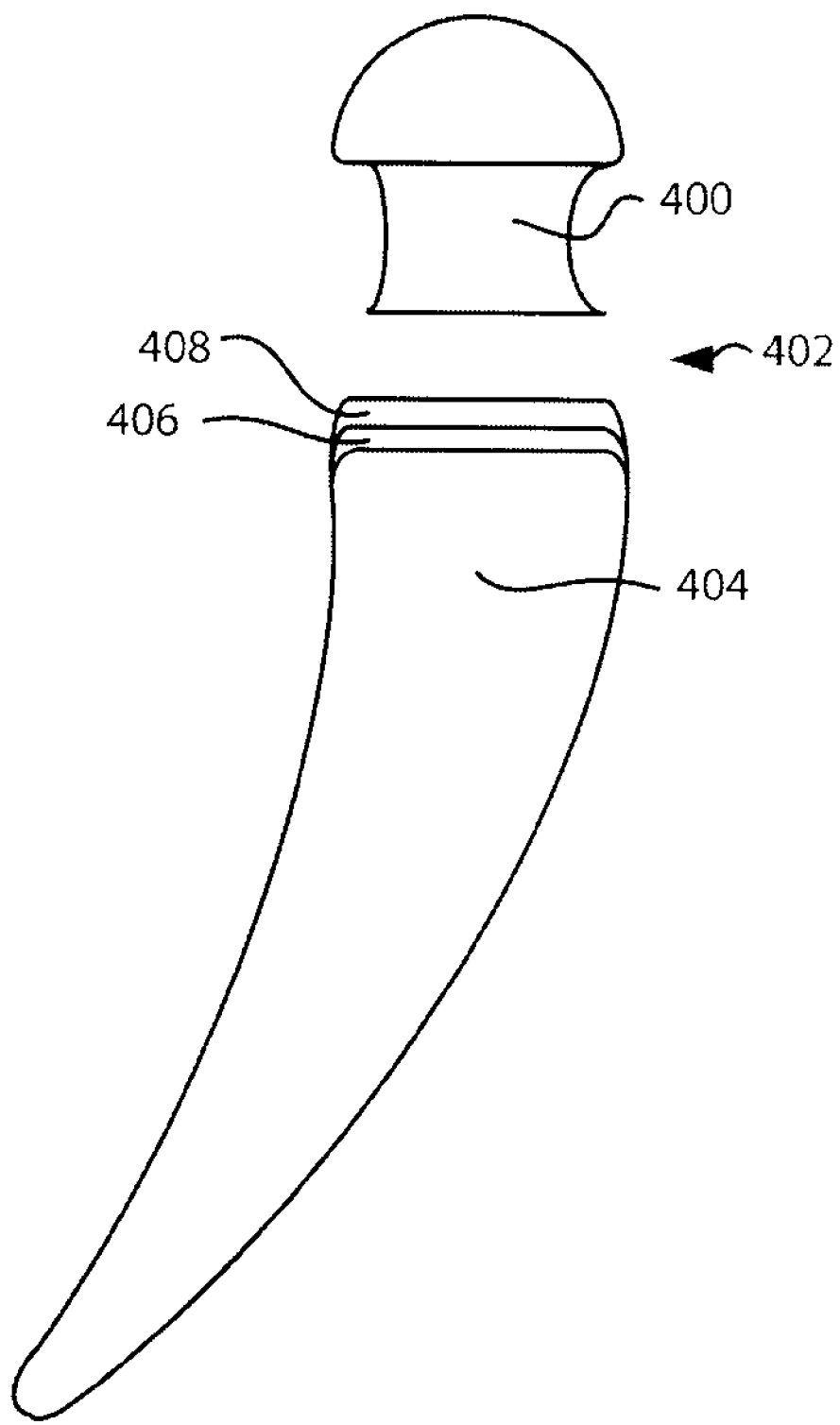
FIG. 4 illustrates an alternate application of the present invention.

With reference to FIG. 4, according to another embodiment of the invention, the present invention could be used to provide improved bonding of a first portion 400 of a prosthetic device 402 to a second portion 404 of the device 402. For example, the first portion 400 might be constructed primarily of hard, dense material such as Co—Cr, while the second portion 404 might be constructed of a porous material such as porous Ti. Heretofore, bonding of porous Ti with a material such as Co—Cr has achieved poor results. In addition, bonding porous Ti with Co—Cr, resulted in galvanic corrosion across the two dissimilar metals.

According to the present invention, a corrosion barrier layer 406 can be deposited onto the first portion 400 by laser based metal deposition (LBMD). Thereafter, a layer of Co—Cr 408 can be deposited onto the corrosion barrier layer, again by LBMD deposition. Co—Cr can be bonded very well with Co—Cr. Therefore, the LBMD deposited Co—Cr outer surface 408 of the second portion 404 can achieve excellent bonding with the Co—Cr of the first portion 400 without any corrosion problems.

Figure 5:
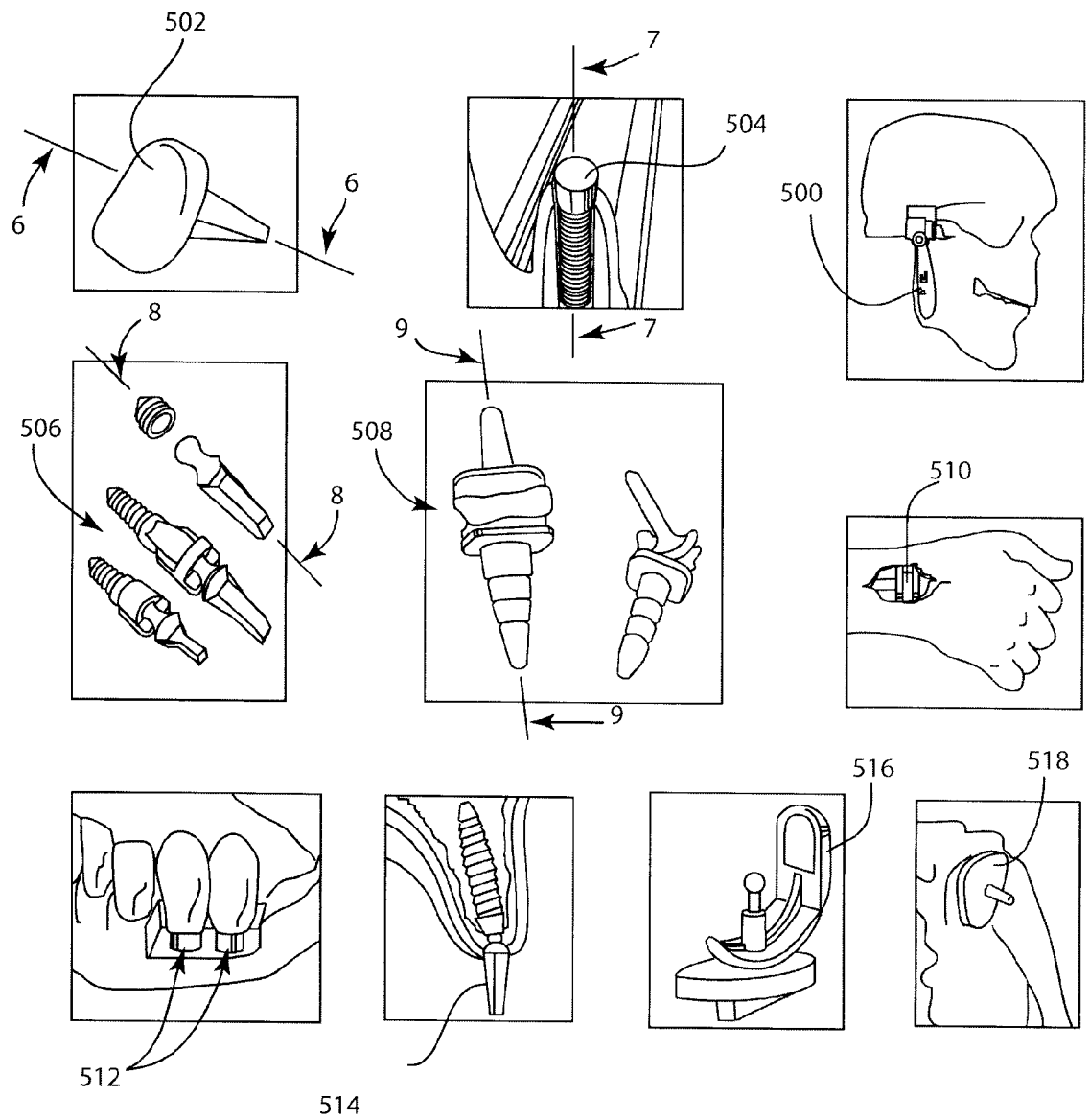
FIG. 5 shows various implants that could have improved bone ingrowths or bearing properties if processed by LBMD.

FIG. 5 illustrates by way of example and not limitation, various other possible devices in which the present invention might be embodied. Devices shown in FIG. 5 include a TMJ joint 500 in situ, an implant for the great toe 502 (also generally representative of knee, wrist and spinal implants), a dental implant 504 in situ, articulating finger implants 506, thumb implants 508, a wrist implant 510 in situ, dental implants 512 in situ, a dental implant 514 in situ, a knee implant 516, and a shoulder implant 518 in situ. More detail about each of these implants is set forth below.

Figure 6:
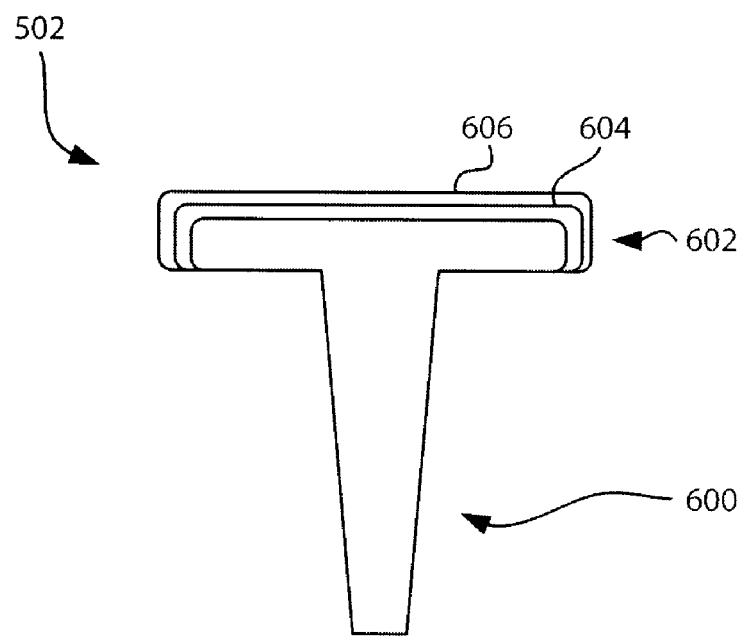
FIG. 6 is a partial cross sectional view of the toe implant of FIG. 5 taken along line 6-6 of FIG. 5.

FIG. 6 is a partial cross sectional view of the toe implant 502 of FIG. 5 taken along line 6-6 of FIG. 5. As shown, the implant 502 has a shank 600 and a knuckle portion 602 formed from a unitary body of porous material such as tantalum. The porous shank 600 remains exposed for fusion with bone. However, because the knuckle portion 602 is designed to engage a corresponding knuckle of bone, metal or ceramic, the knuckle portion 602 has a smooth outer surface that must be resistant to wear. Using the LBMD process described above, a corrosion resistant layer 604 of corrosion-resistant material (e.g., Ti) is formed on at least a portion of the knuckle portion. An outer layer 606 of a wear resistant material (e.g., Co—Cr alloy) is formed over the corrosion resistant layer 604.

Figure 7:
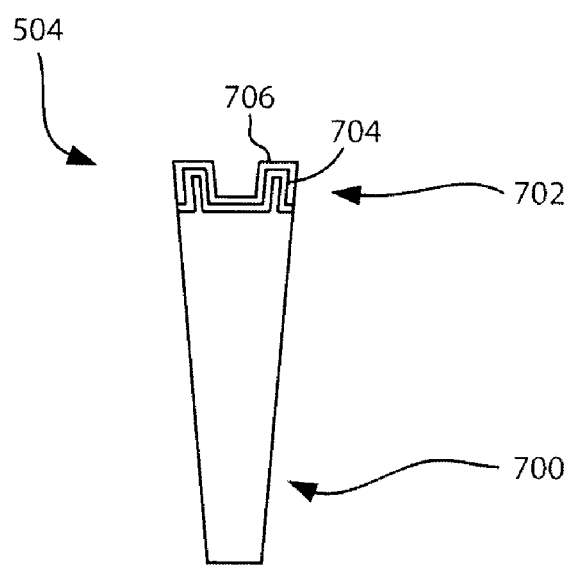
FIG. 7 is a partial cross sectional view of the dental implant of FIG. 5 taken along line 7-7 of FIG. 5.

FIG. 7 is a partial cross sectional view of the dental implant 504 of FIG. 5 taken along line 7-7 of FIG. 5. As shown, the implant 504 has a shank 700 and a tooth coupling portion 702 formed from a unitary body of porous material such as tantalum. The porous shank 700 remains exposed for fusion with the jaw bone. However, because the tooth coupling portion 702 is designed to engage an artificial tooth, the tooth coupling portion 702 must be resistant to wear created by the stresses of chewing food. Using the LBMD process described above, a corrosion resistant layer 704 of corrosion-resistant material (e.g., Ti) is formed on at least a portion of the tooth coupling portion 702. An outer layer 706 of a wear resistant material (e.g., Co—Cr alloy) is formed over the corrosion resistant layer 704.

Note that an implant similar to the implant 504 of FIG. 7 can be used with the TMJ joint 500 of FIG. 5 to secure the TMJ joint to the jaw and cranium of the host patient. In that case, the implant would be formed of a unitary body of porous material for fusion with bone, the portion of the implant engaging the hinged members would have the corrosion resistant layer and durable outer layer formed thereon by the LBMD process. The durable outer layer would resist wear between the implant and the hinged member caused by the stresses of chewing.

Figure 8:
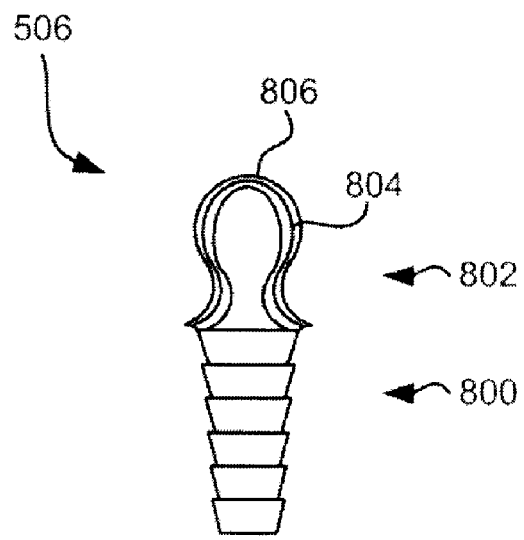
FIG. 8 is a partial cross sectional view of one articulating implant of FIG. 5 taken along line 8-8 of FIG. 5.

FIG. 8 is a partial cross sectional view of one articulating implant 506 of FIG. 5 taken along line 8-8 of FIG. 5. As shown, the implant 506 has a shank 800 and a ball portion 802 formed from a unitary body of porous material such as tantalum. The porous shank 800 remains exposed for fusion with the finger bone. However, because the ball portion 802 is designed to engage a corresponding metal socket, the ball portion 802 must be resistant to wear. Using the LBMD process described above, a corrosion resistant layer 804 of corrosion-resistant material (e.g., Ti) is formed on at least a portion of the ball portion 802. An outer layer 806 of a wear resistant material (e.g., Co—Cr alloy) is formed over the corrosion resistant layer 804.

Figure 9:
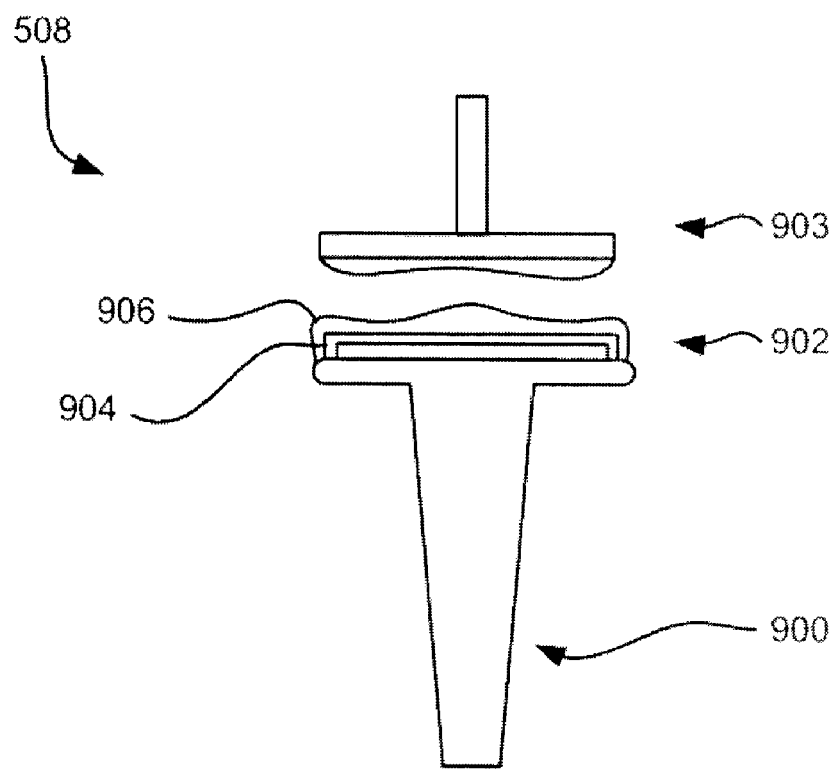
FIG. 9 is a partial cross sectional view of the thumb implant 508 of FIG. 5 taken along line 9-9 of FIG. 5.

FIG. 9 is a partial cross sectional view of the thumb implant 508 of FIG. 5 taken along line 9-9 of FIG. 5. As shown, the implant 508 has a shank 900 and a knuckle portion 902. Here, the shank 900 is formed of hydroxy apatite. The knuckle portion 902 is made of metal coupled to the shank 900. The porous shank 900 remains exposed for fusion with bone. However, because the knuckle portion 902 is designed to engage a corresponding knuckle 903, the knuckle portion 902 has a smooth outer surface that must be resistant to wear. Using the LBMD process described above, a corrosion resistant layer 904 of corrosion-resistant material (e.g., Ti) is formed on at least a portion of the knuckle portion. An outer layer 906 of a wear resistant material (e.g., Co—Cr alloy) is formed over the corrosion resistant layer 904.

FIG. 10 depicts the knee implant 516 of FIG. 5. In this embodiment, a multi-layer structure 1000 is independently formed for insertion in the depression 1002 of the implant 516. The multi-layer structure 1000 is formed of a first layer 1004 of Co—Cr, a middle layer 1006 of corrosion resistant material (e.g., Ti), and an outer layer 1008 of a porous material (e.g., Ta). The multi-layer structure can be fusion or diffusion bonded to the implant 516 that has been made by traditional methods. For example, the Co—Cr surface 1004 of a 0.200 inch three layer structure can be diffusion bonded to the implant 516. The porous surface of the outer layer 1008 is then advantageously available for coupling to bone of a host patient. A description of how to form such multi-layer structures and how to couple them to implants has been provided above.

Figure 11:
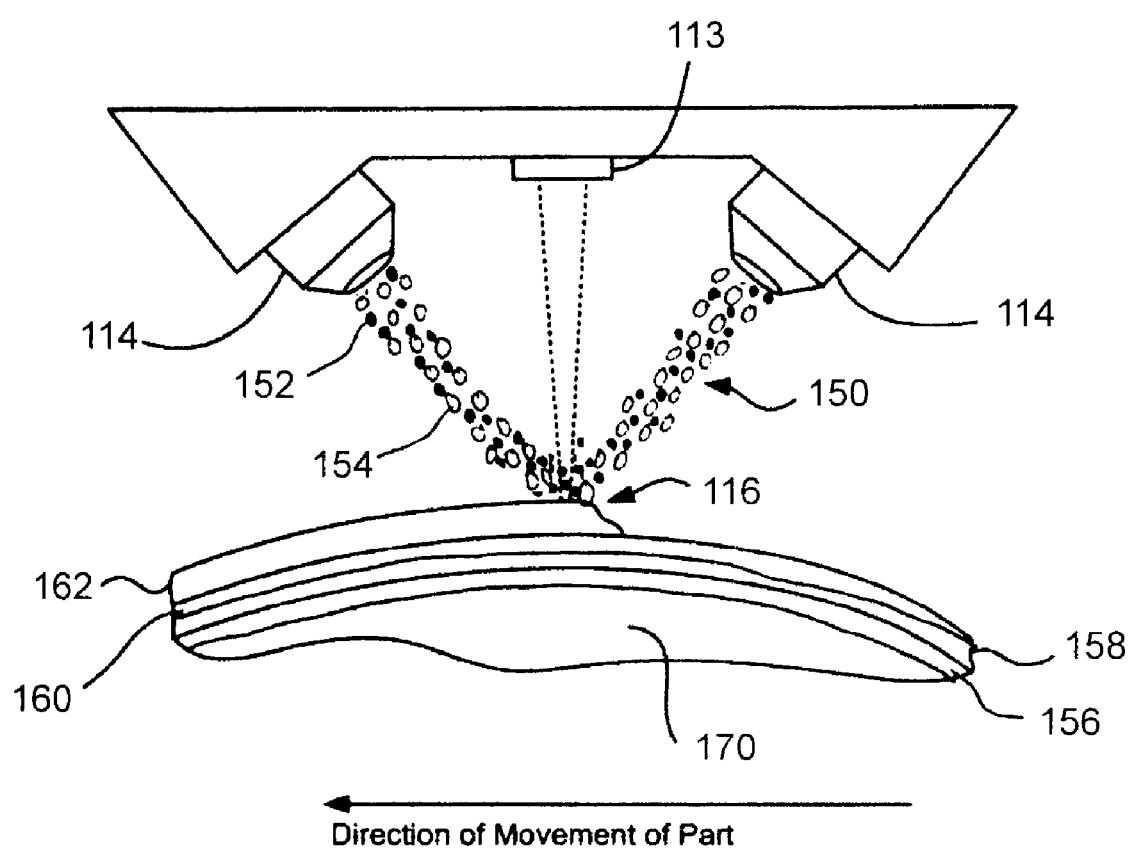
FIG. 11 illustrates the deposition of multiple layers of a powder material blend using LBMD.

Another embodiment of the invention is the deposition of an articulating bearing material in the form of a composite coating in multiple functionally graded layers, in order to enhance the coating performance. FIG. 11 illustrates deposition of a blended material 150 in multiple layers onto a metal base structure 170. In this example, a Ti/TiC composite coating containing 60% TiC (by volume) is deposited on a pre-manufactured Ti-6Al-4V implant material. A powder material blend 150 of a first material 152 comprising 40 Vol. % CP Ti (+100/−325 mesh) and a second material 154 comprising 60% TiC (+100/−325 mesh) is prepared by thoroughly mixing the constituent powders using ball milling or similar powder mixing techniques. The deposition process begins with directing a focused Nd-YAG laser beam 113 onto a substrate 170 placed on the build platform capable of computer-controlled motion. The computer (not shown) utilizes a deposition file which specifies optimal deposition parameters along with required coating thickness and deposition area profiles. Deposition parameters include: laser power, scan speed, scan spacing, scan orientation, layer thickness, powder feed rate, and others. Required coating thickness includes desired final coating thickness plus any machining allowance.

The laser 113 generates a small molten pool (typically 0.25-1 mm in diameter and 0.1-0.5 mm in depth) 116 on the substrate 170. Precise amounts of the powder material blend 150 are injected directly through nozzles 114 into the melt pool 116 using a powder feeder (not shown). The molten pool 116 solidifies rapidly as the laser beam 113 moves away, forming a thin track of solidified metal welded to the material below along the line of laser scanning. A layer 156 of coating is generated by a number of consecutive overlapping tracks. A second layer 158 is generated in the same way, by a series of consecutive overlapping tracks, as are additional layers 160, 162. After each layer is formed, the laser head 113, along with the powder delivery nozzle 114, moves upward by one layer thickness and the subsequent layer is generated. This process is repeated until a coating, composed of multiple functionally graded layers, of desired thickness is deposited. In this example, four layers are deposited; however any number of layers from one on up can be deposited, depending on properties desired for the use of the implant. The deposition process occurs inside an enclosed chamber filled with argon to prevent oxidation of the liquid metal. The part building process is fully automatic and can run unattended.

Figure 12:
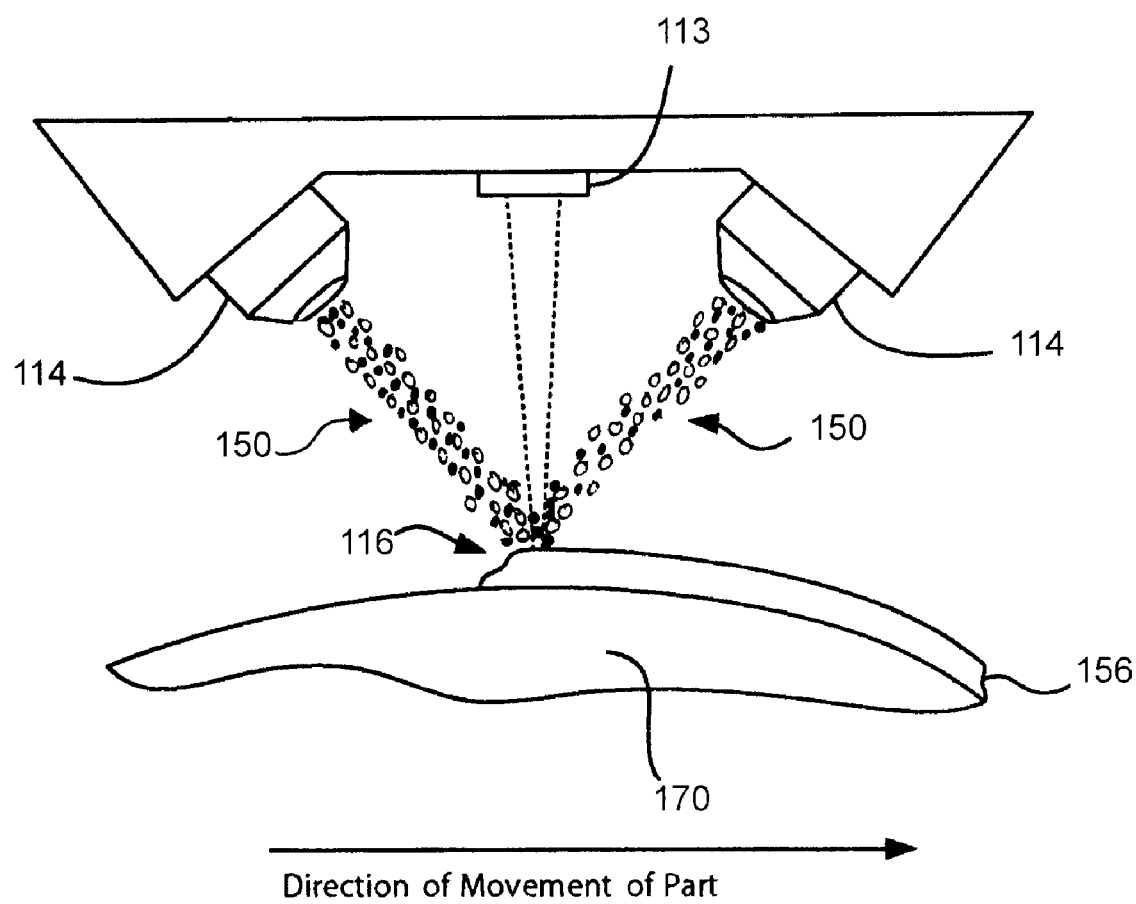
FIG. 12 illustrates the deposition of a single layer of the powder material blend using LBMD.
Figure 13:
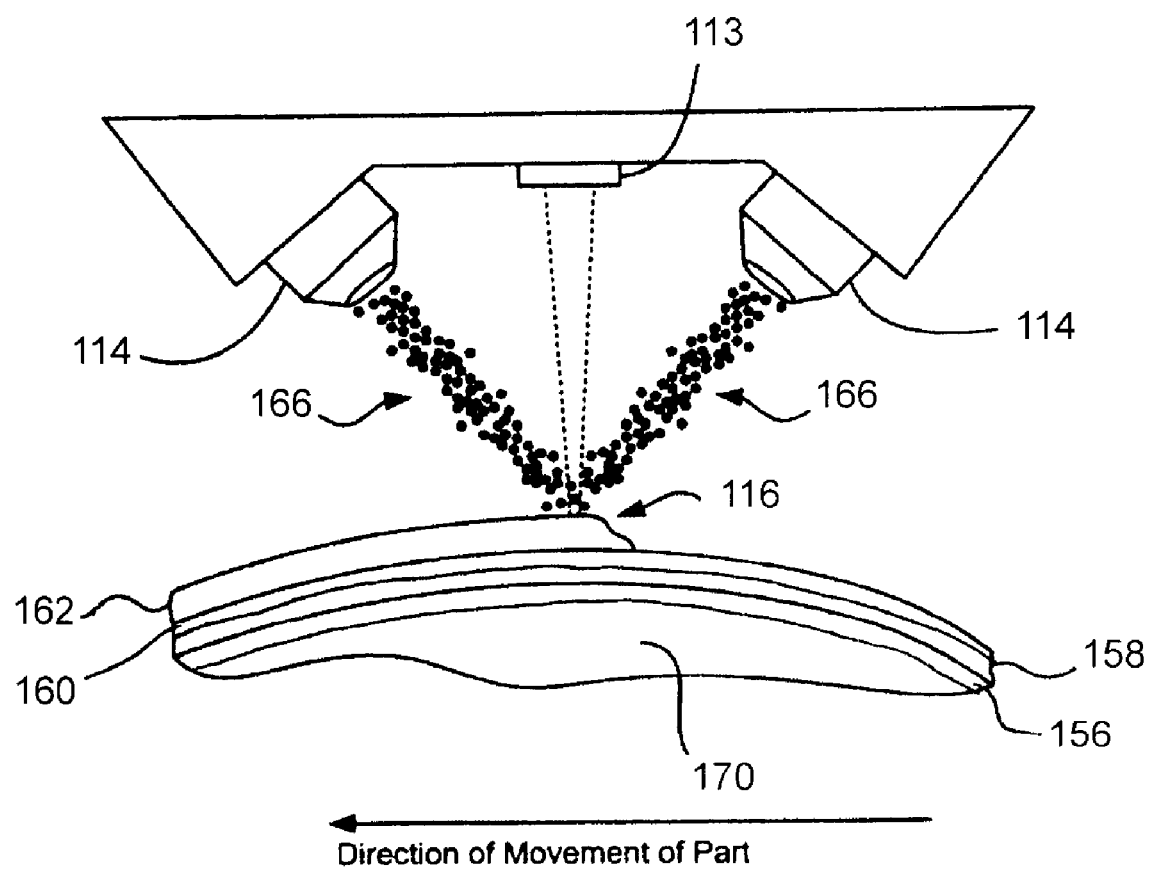
FIG. 13 illustrates the deposition of multiple layers of the first material using LBMD.

FIG. 12 illustrates a variation on the above process, in which the articulating bearing powder material blend 150 is deposited in a single layer 156 upon the base structure 170. This technique could be used when a very thin layer of coating is desired, depending on the type and use of the implant. FIG. 13 illustrates a variation in which a first articulating bearing material 166 instead of the blend is used, but is deposited in a series of layers 156, 158, 160, 162, forming layers of the articulating bearing material on the base structure 170.

Figure 14:
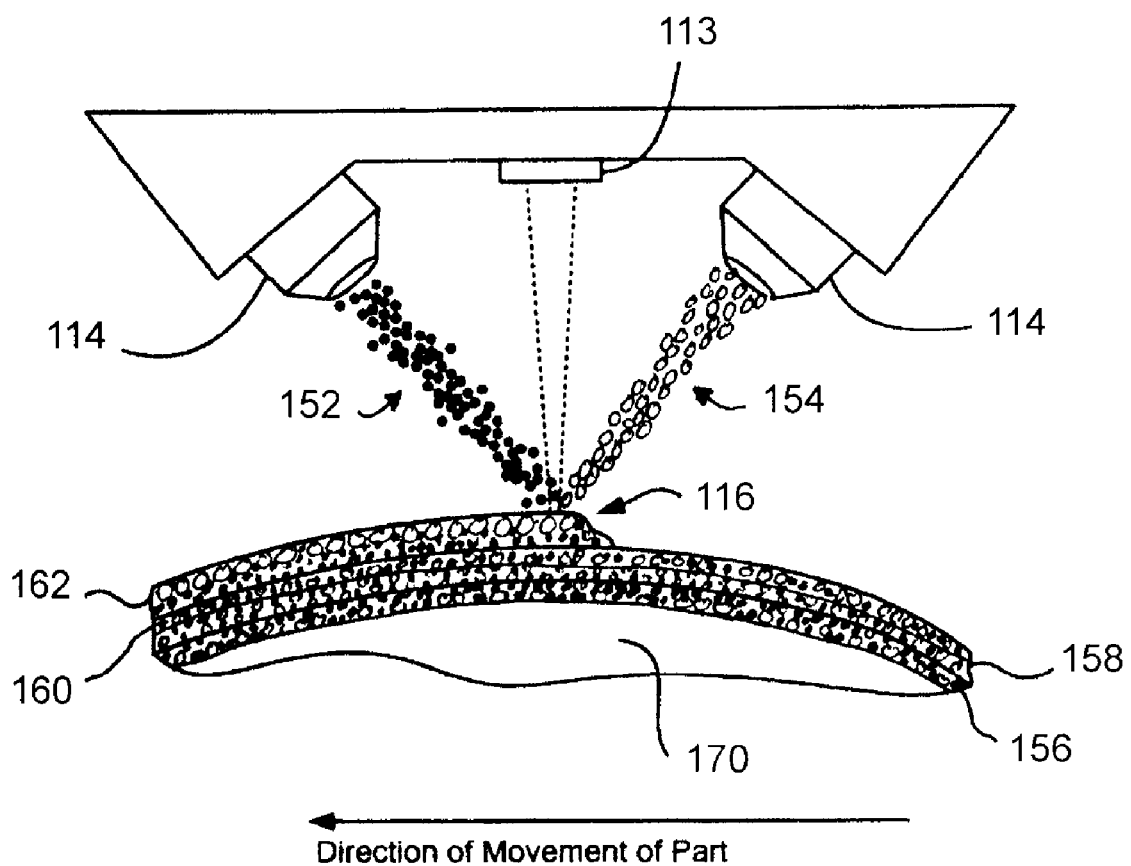
FIG. 14 illustrates the deposition of functionally graded layers of the first material D by one nozzle and the second material by another nozzle using LBMD.

Referring to FIG. 14, a combination of the first material 152 and the second material 154 are deposited in multiple layers upon the base structure 170. One nozzle 114 delivers the first material 152, such as Titanium, as the other nozzle 114 delivers the second material 154, such as Titanium carbide. As each successive layer 156, 158, 160, 162 is deposited, the computer controls the distribution of the first and second materials 152, 154, varying them by layer to produce functionally graded layers.

In the embodiments illustrated in FIGS. 11, 12, 13 and 14 the articulating bearing material is deposited on a base structure 170. The base structure 170 could be, but is not limited to, a hip implant, a TMJ joint implant, an implant for the great toe, a knee implant, a wrist implant, spiral implants, a dental implant, an articulating finger implant, a thumb implant, and a shoulder implant. In addition, the process used to deposit the articulating bearing material can include, but is not limited to any energy source that can provide sufficient energy locally to melt and deposit the additive material, such as LBMD, plasma, or electron beam energy. A welding based cladding process may also be used. Also, the first and second materials, their particle sizes and distributions may be varied to produce different microstructural coatings, depending upon the desired coating characteristics for the specific application.

Another embodiment of the invention includes the deposition of an antimicrobial material in combination with the metal base material, onto the implant base structure. One antimicrobial material may be silver in the form of elemental silver, a silver salt or a silver intermetallic. The antimicrobial properties of silver have been well documented, with numerous studies measuring the efficacy of silver in the reduction of bacteria including *Escherichia coli, Staphylococcus aureus*, and *Staphylococcus epidermis*, among others. However, other suitable antimicrobial materials may be used in place of silver, including but not limited to gold, platinum, palladium, iridium, copper, tin, antimony, bismuth, zinc, salts thereof, and intermetallics thereof.

Figure 15:
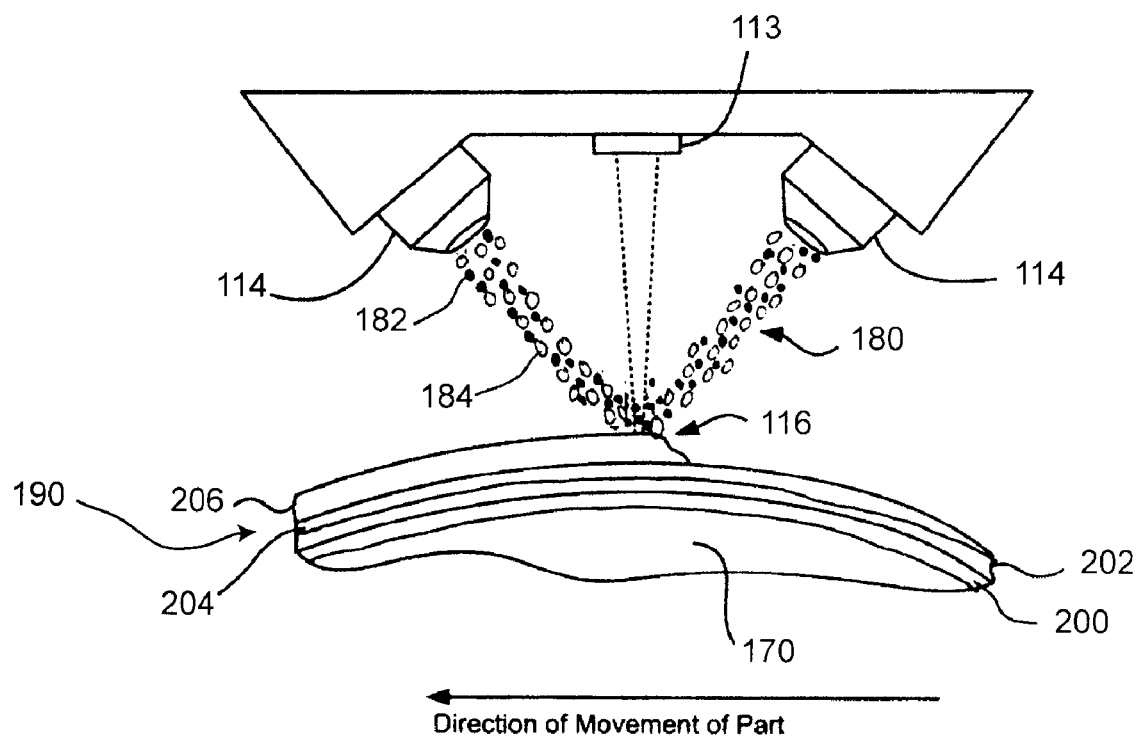
FIG. 15 illustrates the deposition of multiple layers of a blend of an antimicrobial material and a first metal using LBMD.

FIG. 15 illustrates the deposition of a combination of a metal and an antimicrobial material onto the surface of an implant. A blend 180 of a first metal 182 and an antimicrobial material 184 is directed in streams from the nozzles 114 to the surface of the base structure 170. The first metal 182 may be the same metal which forms the base structure 170, and may comprise cobalt-chrome, tantalum, titanium, platinum, zirconium, niobium, stainless steel, or an alloy thereof. The antimicrobial material 184 may be elemental silver, a silver salt, a silver intermetallic, or any other antimicrobial metal or material which is suitable to be combined with the first metal 182. The laser 113 melts the blend 180, creating the melt pool 116. The molten pool 116 solidifies rapidly as the laser beam 113 moves away, forming a thin track of solidified blend 180 welded to the material below along the line of laser scanning. A layer 200 of the deposit is generated by a number of consecutive overlapping tracks. A second layer 202 is generated in the same way, by a series of consecutive overlapping tracks, as are additional layers 204, 206. Alter each layer is formed, the laser head 113, along with the powder delivery nozzles 114, move upward by one layer thickness and the subsequent layer is generated. When all layers have been deposited, a multi-layered deposit 190 remains on the surface of the base structure 170.

Figure 16:
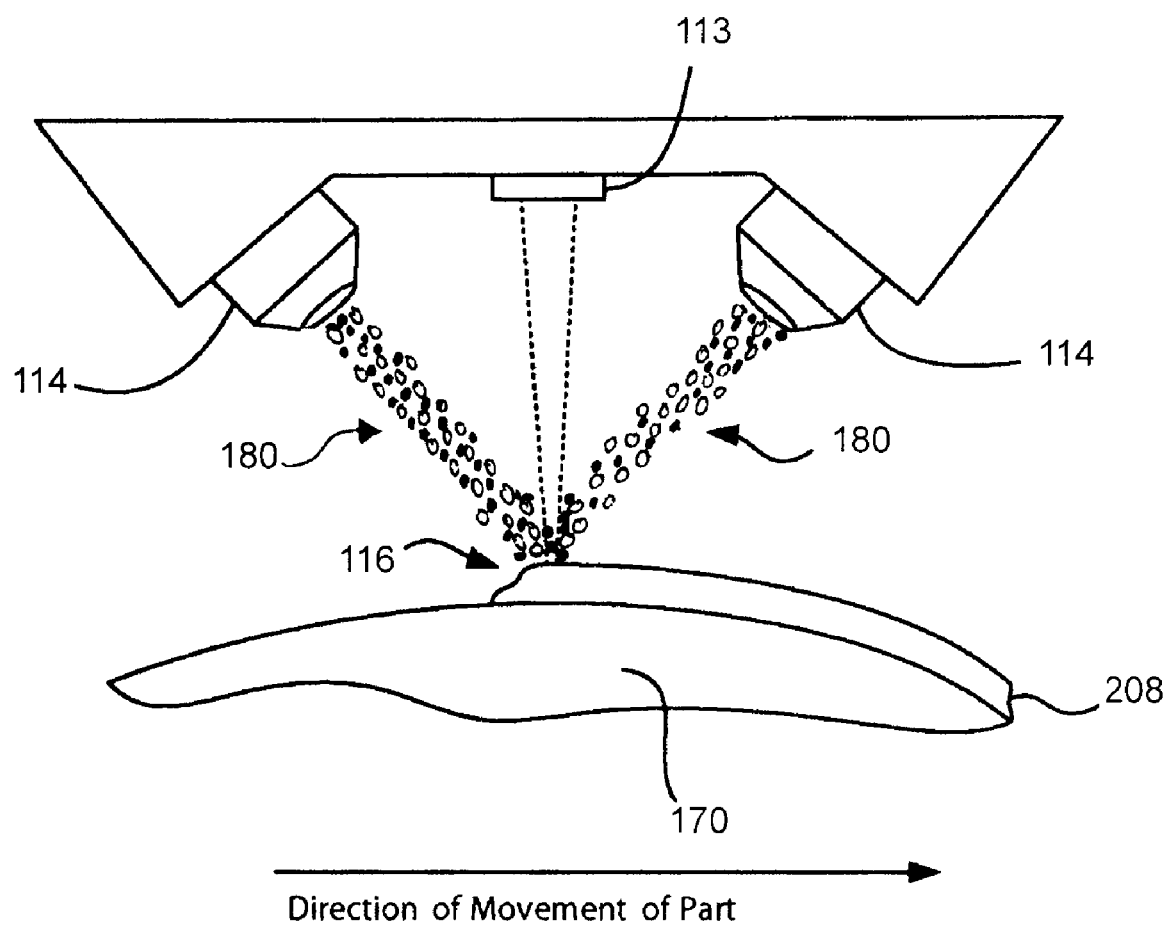
FIG. 16 illustrates the deposition of single layer of the blend of the antimicrobial material and the first metal using LBMD.

FIG. 16 illustrates a variation on the above process, in which the antimicrobial material blend 180 is deposited in a single layer 208 upon the base structure 170. This technique could be used when a very thin deposit is desired, depending on the type and use of the implant. A deposit as thin as 25 microns may be created by this process. Post deposition processes which include but are not limited to annealing, etching in acid or base, or oxygen plasma can be used to control the layer thickness below 25 microns, as well as control surface porosity.

Figure 17:
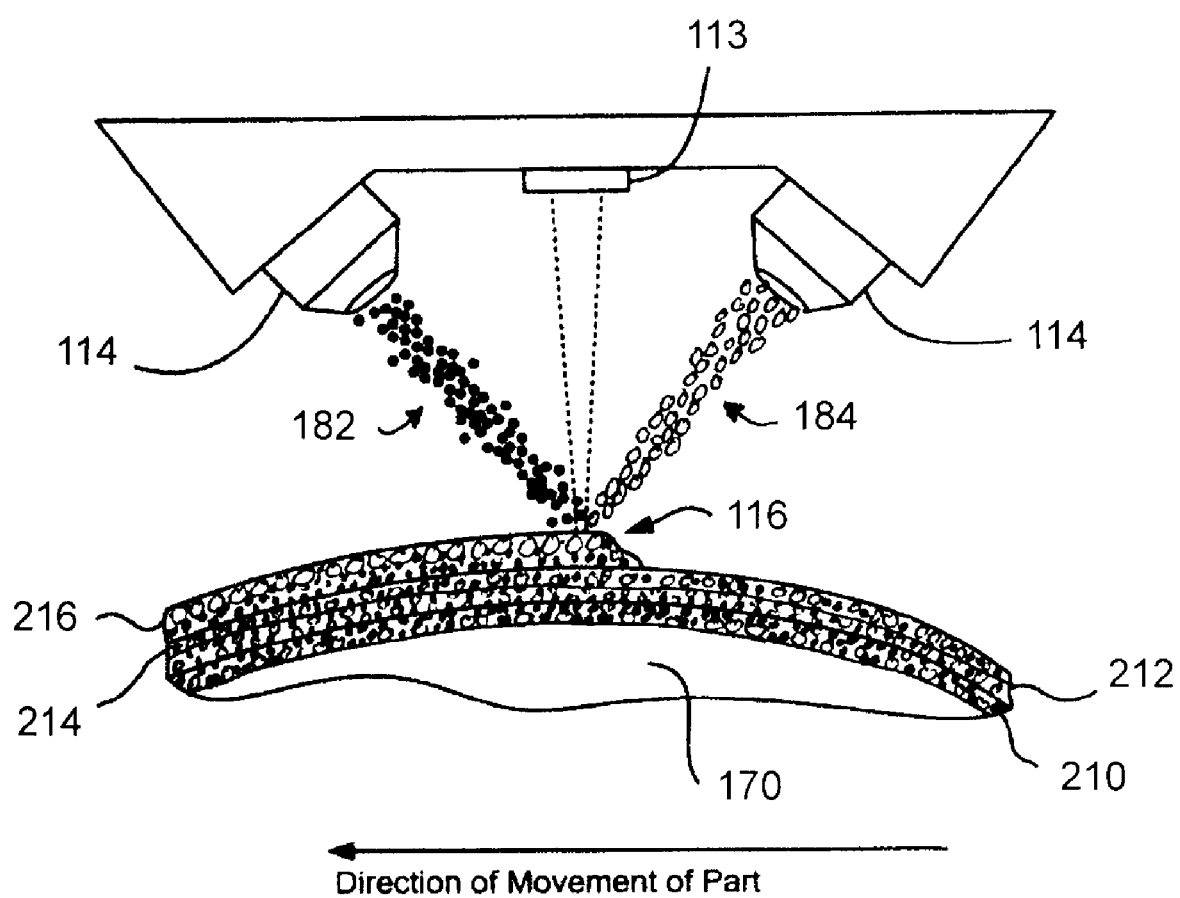
FIG. 17 illustrates the deposition of functionally graded layers of the antimicrobial material and the first metal using LBMD.

The antimicrobial material 184 and first metal 182 may also be deposited in functionally graded layers. Referring to FIG. 17, a combination of the first metal 182 and the antimicrobial material 184 are deposited in multiple layers upon the base structure 170. One nozzle 114 delivers the first metal 182, such as titanium, as the other nozzle 114 delivers the antimicrobial material 184, such as elemental silver. As each successive layer 210, 212, 214, and 216 is deposited, the computer controls the distribution of the first metal 182 and antimicrobial material 184, varying them by layer to produce functionally graded layers.

Such functionally graded layers can be used to accomplish a number of different results. According to one example, the concentration of the antimicrobial material 184 may gradually increase as new layers are added so that the outermost layers possess the most potent antimicrobial properties. According to another example, the harder of two materials being combined may be deposited in greater concentrations as successive layers are formed to provide an increased hardness of the outermost layers. Such a structure may be particularly useful for the formation of articular surfaces. According to another example, the more porous of two materials being combined may be deposited in greater concentrations as successive layers are formed to provide an increased porosity of the outermost layers. Such a structure may be particularly useful for the formation of bone in-growth surfaces.

Combinations of the above-described examples are also possible. Additionally, more than two different materials may be combined; such materials may be deposited in functionally graded layers that accomplish multiple desirable property changes along the thickness of the coating. Such functional gradients may be employed regardless of whether any of the materials being deposited has antimicrobial properties.

Figure 18:
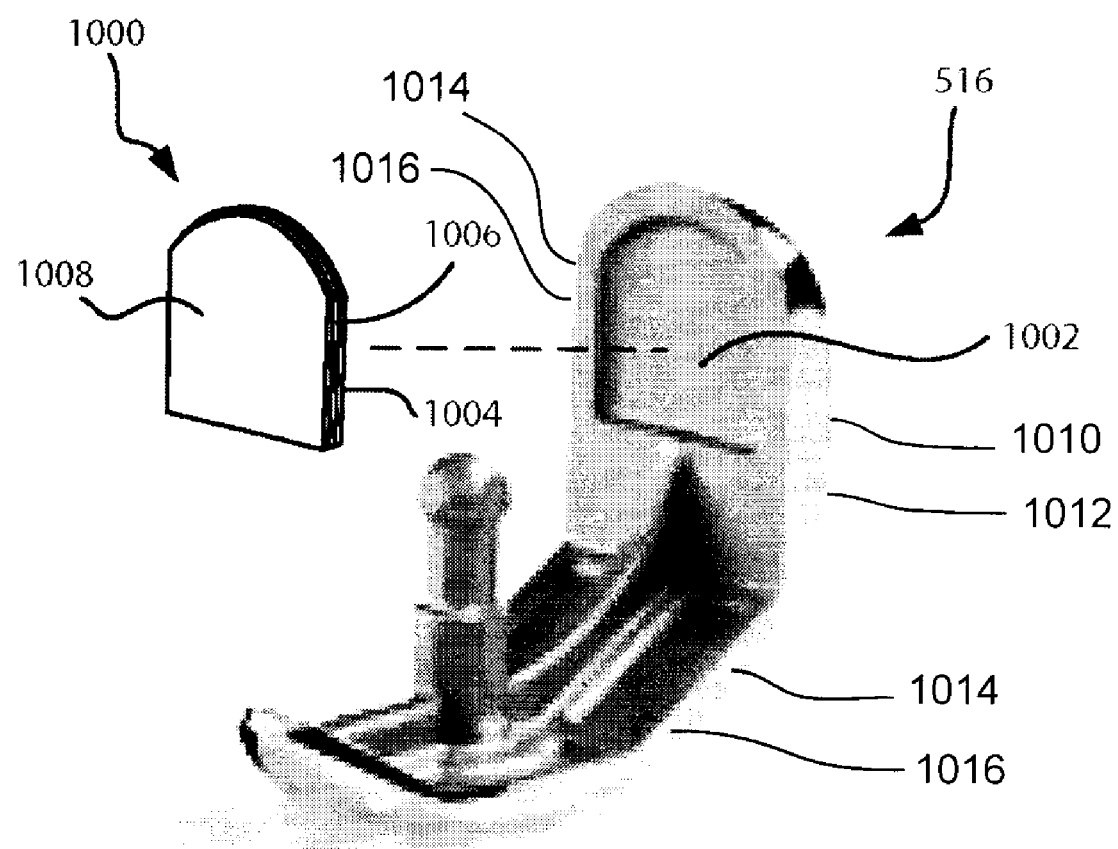
FIG. 18 is perspective view of the knee implant of FIG. 10 showing zone-specific deposits of bearing surface material, porous bone ingrowth material and antimicrobial material.

FIG. 18 illustrates another embodiment of the invention, in which a plurality of zone-specific deposits comprising different compositions is made on the same base structure, in this example a knee implant. The depression 1002 of the implant 516 is shaped to hold the multi-layer structure 1000, which comprises a deposited outer layer 1008 of a porous bone ingrowth material. On an anterior curved surface 1010 of the implant 516, a deposited outer layer 1012 comprising a bearing surface material such as titanium carbide is formed by the LBMD process. On lateral edges 1014 on either lateral side of the implant 516, a deposited outer layer 1016 comprising an antimicrobial material is formed by the LBMD process. The lateral edges 1014 are not designed for articulation or bone apposition, but may instead help to reduce the likelihood of infection of the surrounding tissues due to the antimicrobial of the deposited outer layer 1016.

In other examples, antimicrobial material may be combined with either the porous bone ingrowth material, or the bearing surface material, or both, and deposited on the implant. It is appreciated that various combinations of base structure material, porous bone ingrowth material, bearing surface material, and antimicrobial material may be made and deposited on the implant, depending on the desired characteristics for the particular zone of the implant surface, be it bone ingrowth, bearing, antimicrobial, or a combination thereof. Furthermore, enhancing hardness, porosity, or antimicrobial properties are not the only functions that may be served by biomedical implant coatings formed via LBMD; indeed, such coatings may help to enhance biocompatibility of the implant, provide a desired level of radio-opacity, or even provide functional geometrical shapes that may be used for interconnection with other implants, bone anchorage, or other purposes.

While the present invention has been disclosed in its preferred form, the specific embodiments thereof as disclosed and illustrated herein are not to be considered in a limiting sense, as numerous variations are possible. The invention may be embodied in other specific forms without departing from its spirit or essential characteristics. No single feature, function, element or property of the disclosed embodiments is essential. The scope of the invention is, therefore, indicated by the appended claims rather than by the foregoing description.

The invention claimed is:

1. A method for constructing a biomedical implant, the method comprising:
   forming a base structure from a metal material; and
   depositing on the base structure a deposit in functionally graded layers, the deposit comprising an antimicrobial material and a first metal, wherein the outermost layers possess the most potent antimicrobial properties, wherein depositing the deposit is accomplished in an inert gas atmosphere.

2. A method as in claim 1, wherein the antimicrobial material comprises at least one of elemental silver, gold, platinum, palladium, iridium, copper, tin, antimony, bismuth, zinc, salts thereof, or intermetallics thereof.

3. A method as in claim 1, wherein the first metal comprises at least one of cobalt-chrome, tantalum, titanium, platinum, zirconium, niobium, stainless steel, or alloys thereof.

4. A method as in claim 1, further comprising depositing the deposit with a thickness greater than 25 microns.

5. A method as in claim 1, further comprising modifying the deposit by a process selected from the group consisting of annealing, etching in acid, etching in base, and oxygen plasma.

6. A method for constructing a biomedical implant, the method comprising:
   forming a base structure from a metal material; and
   depositing a deposit onto the metal base structure-by Laser Based Metal Deposition (LBMD) in an inert gas atmosphere, wherein the deposit comprises an antimicrobial material and a first metal, wherein depositing the deposit comprises functionally graded layers, wherein the outermost layers possess the most potent antimicrobial properties.

7. A method as in claim 6, wherein the antimicrobial material comprises at least one of elemental silver, gold, platinum, palladium, iridium, copper, tin, antimony, bismuth, zinc, salts thereof, or intermetallics thereof.

8. A method as in claim 6, wherein the first metal comprises at least one of cobalt-chrome, tantalum, titanium, platinum, zirconium, niobium, stainless steel, or alloys thereof.

9. A method as in claim 6, wherein depositing the deposit further comprises selecting the metal base structure comprising a base shaped to be secured to a body part of a patient.

10. A method as in claim 6, further comprising depositing the deposit with a thickness greater than 25 microns.

11. A method as in claim 6, further comprising modifying the deposit by a process selected from the group consisting of annealing, etching in acid, etching in base, and oxygen plasma.

12. A method for constructing a biomedical implant, the method comprising:
    forming a base structure from a biocompatible metal material;
    selecting at least one selection from the group consisting of a first metal, an antimicrobial material, a porous bone ingrowth material, a bearing material, and combinations thereof; and
    depositing at least one deposit comprising the selection onto the metal base structure by Laser Based Metal Deposition (LBMD) in an inert gas atmosphere and in functionally graded layers, wherein the outermost layers possess the most potent antimicrobial properties.

13. A method as in claim 12, wherein the antimicrobial material comprises at least one of elemental silver, gold, platinum, palladium, iridium, copper, tin, antimony, bismuth, zinc, salts thereof, or intermetallics thereof.

14. A method as in claim 12, wherein the first metal comprises at least one of cobalt-chrome, tantalum, titanium, platinum, zirconium, niobium, stainless steel, or alloys thereof.

15. A method as in claim 12, wherein the first metal comprises at least one of cobalt-chrome, tantalum, titanium, platinum, zirconium, niobium, stainless steel, or alloys thereof.

16. A method as in claim 12, further comprising selecting the bearing material of a biocompatible composition comprising cobalt and chromium.

17. A method as in claim 12, wherein depositing at least one deposit further comprises selecting the metal base structure comprising a base shaped to be secured to a body part of a patient.

18. A method as in claim 12, further comprising depositing each deposit with a thickness greater than 25 microns.

19. A method as in claim 12, further comprising modifying the deposit by a process selected from the group consisting of annealing, etching in acid, etching in base, and oxygen plasma.

20. A method for constructing a biomedical implant, the method comprising:
    forming a base structure from a biocompatible metal material; and
    depositing on the base structure a deposit to provide a surface other than a bone apposition surface or an articular surface via Laser Based Metal Deposition (LBMD) in an inert gas atmosphere, wherein depositing the deposit to provide the surface comprises positioning the surface to contact a non-articulating non-bony tissue adjacent to the implant.

21. The method of claim 20, wherein depositing the deposit comprises depositing an antimicrobial material.

22. The method of claim 21, further comprising depositing at least one deposit in functionally graded layers wherein the outermost layers possess the most potent antimicrobial properties.

23. The method of claim 20, wherein the antimicrobial material comprises at least one of elemental silver, gold, platinum, palladium, iridium, copper, tin, antimony, bismuth, zinc, salts thereof, or intermetallics thereof.

24. The method of claim 20, wherein the first metal comprises at least one of cobalt-chrome, tantalum, titanium, platinum, zirconium, niobium, stainless steel, or alloys thereof.

25. The method of claim 20, wherein depositing the deposit further comprises selecting the metal base structure comprising a base shaped to be secured to a body part of a patient.

26. The method of claim 20, further comprising depositing at least one deposit in functionally graded layers.

27. A method for constructing a biomedical implant, the method comprising:
forming a base structure from a metal material; and
depositing on the base structure a deposit comprising an antimicrobial material and a first metal, wherein depositing the deposit is accomplished in an inert gas atmosphere, wherein the antimicrobial material comprises at least one of elemental silver, gold, platinum, palladium, iridium, copper, tin, antimony, bismuth, zinc, salts thereof, or intermetallics thereof.

28. A method as in claim 27, wherein the first metal comprises at least one of cobalt-chrome, tantalum, titanium, platinum, zirconium, niobium, stainless steel, or alloys thereof.

29. A method as in claim 27, further comprising depositing the deposit with a thickness greater than 25 microns and modifying the deposit by a process selected from the group consisting of annealing, etching in acid, etching in base, and oxygen plasma.

30. A method for constructing a biomedical implant, the method comprising:
forming a base structure from a metal material; and
depositing a deposit comprising an antimicrobial material and a first metal onto the metal base structure by Laser Based Metal Deposition (LBMD) in an inert gas atmosphere, wherein the antimicrobial material comprises at least one of elemental silver, gold, platinum, palladium, iridium, copper, tin, antimony, bismuth, zinc, salts thereof, or intermetallics thereof.

31. A method as in claim 30, wherein the first metal comprises at least one of cobalt-chrome, tantalum, titanium, platinum, zirconium, niobium, stainless steel, or alloys thereof.

32. A method as in claim 30, wherein depositing the deposit further comprises selecting the metal base structure comprising a base shaped to be secured to a body part of a patient.

33. A method as in claim 30, further comprising depositing the deposit with a thickness greater than 25 microns and modifying the deposit by a process selected from the group consisting of annealing, etching in acid, etching in base, and oxygen plasma.

34. A method for constructing a biomedical implant, the method comprising:
forming a base structure from a metal material;
depositing a deposit comprising an antimicrobial material and a first metal onto the metal base structure by Laser Based Metal Deposition (LBMD) in an inert gas atmosphere; and
modifying the deposit by a process selected from the group consisting of annealing, etching in acid, etching in base, and oxygen plasma.

35. A method as in claim 34, further comprising selecting the bearing material of a biocompatible composition comprising cobalt and chromium, and wherein the antimicrobial material comprises at least one of elemental silver, gold, platinum, palladium, iridium, copper, tin, antimony, bismuth, zinc, salts thereof, or intermetallics thereof, and wherein the first metal comprises at least one of cobalt-chrome, tantalum, titanium, platinum, zirconium, niobium, stainless steel, or alloys thereof.

36. A method as in claim 34, wherein depositing at least one deposit further comprises selecting the metal base structure comprising a base shaped to be secured to a body part of a patient, wherein depositing each deposit with a thickness greater than 25 microns.

37. A method as in claim 34, further comprising depositing the at least one deposit in functionally graded layers wherein the outermost layers possess the most potent antimicrobial properties.

38. A method for constructing a biomedical implant, the method comprising:
forming a base structure from a biocompatible metal material;
selecting at least one selection from the group consisting of a first metal, an antimicrobial material, a porous bone ingrowth material, a bearing material, and combinations thereof, wherein the antimicrobial material comprises at least one of elemental silver, gold, platinum, palladium, iridium, copper, tin, antimony, bismuth, zinc, salts thereof, or intermetallics thereof; and
depositing at least one deposit comprising the selection onto the metal base structure by Laser Based Metal Deposition (LBMD) in an inert gas atmosphere.

39. A method as in claim 38, further comprising selecting the bearing material of a biocompatible composition comprising cobalt and chromium, and wherein the first metal comprises at least one of cobalt-chrome, tantalum, titanium, platinum, zirconium, niobium, stainless steel, and alloys thereof, and wherein the first metal comprises at least one of cobalt-chrome, tantalum, titanium, platinum, zirconium, niobium, stainless steel, or alloys thereof.

40. A method as in claim 38, wherein depositing at least one deposit further comprises selecting the metal base structure comprising a base shaped to be secured to a body part of a patient, wherein depositing each deposit with a thickness greater than 25 microns and modifying the deposit by a process selected from the group consisting of annealing, etching in acid, etching in base, and oxygen plasma.

41. A method for constructing a biomedical implant, the method comprising:
forming a base structure from a biocompatible metal material;
selecting at least one selection from the group consisting of a first metal, an antimicrobial material, a porous bone ingrowth material, a bearing material, and combinations thereof;
depositing at least one deposit comprising the selection onto the metal base structure by Laser Based Metal Deposition (LBMD) in an inert gas atmosphere; and
modifying the deposit by a process selected from the group consisting of annealing, etching in acid, etching in base, and oxygen plasma.

42. A method as in claim 41, further comprising selecting the bearing material of a biocompatible composition comprising cobalt and chromium, and wherein the antimicrobial material comprises at least one of elemental silver, gold, platinum, palladium, iridium, copper, tin, antimony, bismuth, zinc, salts thereof, or intermetallics thereof, and wherein the first metal comprises at least one of cobalt-chrome, tantalum, titanium, platinum, zirconium, niobium, stainless steel, or alloys thereof.

43. A method as in claim 41, wherein depositing at least one deposit further comprises selecting the metal base structure comprising a base shaped to be secured to a body part of a patient, wherein depositing each deposit with a thickness greater than 25 microns.

44. A method as in claim 41, further comprising depositing the at least one deposit in functionally graded layers wherein the outermost layers possess the most potent antimicrobial properties.

45. A method for constructing a biomedical implant, the method comprising:
forming a base structure from a biocompatible metal material; and
depositing on the base structure a deposit to provide a surface other than a bone apposition surface or an articular surface via Laser Based Metal Deposition (LBMD) in an inert gas atmosphere, wherein depositing the deposit comprises depositing an antimicrobial material in functionally graded layers wherein the outermost layers possess the most potent antimicrobial properties.

46. The biomedical implant of claim 45, wherein depositing the deposit to provide the surface comprises positioning the surface to contact a non-articulating non-bony tissue adjacent to the implant.

47. The method of claim 45, wherein the antimicrobial material comprises at least one of elemental silver, gold, platinum, palladium, iridium, copper, tin, antimony, bismuth, zinc, salts thereof, or intermetallics thereof, and wherein the first metal comprises at least one of cobalt-chrome, tantalum, titanium, platinum, zirconium, niobium, stainless steel, or alloys thereof.

48. The method of claim 45, wherein depositing the deposit further comprises selecting the metal base structure comprising a base shaped to be secured to a body part of a patient.

* * * * *

UNITED STATES PATENT AND TRADEMARK OFFICE
CERTIFICATE OF CORRECTION

| | | |
|---|---|---|
| PATENT NO. | : 7,951,412 B2 | Page 1 of 1 |
| APPLICATION NO. | : 11/624041 | |
| DATED | : May 31, 2011 | |
| INVENTOR(S) | : Daniel F. Justin et al. | |

It is certified that error appears in the above-identified patent and that said Letters Patent is hereby corrected as shown below:

Column 18, line 22, cancel the text beginning with "15. A method as in" to and ending "or alloys thereof." in column 18 line 24.

Column 18, line 56, replace "The method of claim 20" with --The method of claim 21--.

Column 18, line 60, cancel the text beginning with "24. The method of" to and ending "or alloys thereof." in column 18 line 62.

Column 19, line 50, cancel the text beginning with "further comprising selecting" to and ending "and chromium, and" in column 19 line 52.

Column 19, lines 59-60, replace "at least one" with --the--.

Column 19, line 62, replace "wherein" with --and--.

Column 19, line 65, cancel the text "at least one".

Column 21, line 6, replace "biomedical implant" with --method--.

Column 22, line 2, cancel the text beginning with ", and wherein the" to and ending "or alloys thereof" in column 22 line 5.

Signed and Sealed this
Fifth Day of June, 2012

David J. Kappos
*Director of the United States Patent and Trademark Office*